(12) United States Patent
Ridder et al.

(10) Patent No.: US 7,616,123 B2
(45) Date of Patent: Nov. 10, 2009

(54) APPARATUS AND METHOD FOR NONINVASIVELY MONITORING FOR THE PRESENCE OF ALCOHOL OR SUBSTANCES OF ABUSE IN CONTROLLED ENVIRONMENTS

(75) Inventors: Trent Ridder, Woddbridge, VA (US); Ben ver Steeg, Redlands, CA (US); James McNally, Albuquerque, NM (US); John D. Maynard, Albuquerque, NM (US); Russell E. Abbink, Sandia Park, NM (US)

(73) Assignee: TruTouch Technologies, Inc., Albuquerque, NM (US)

( * ) Notice: Subject to any disclaimer, the term of this patent is extended or adjusted under 35 U.S.C. 154(b) by 328 days.

(21) Appl. No.: 11/515,565

(22) Filed: Sep. 5, 2006

(65) Prior Publication Data
US 2007/0073118 A1 Mar. 29, 2007

Related U.S. Application Data

(63) Continuation-in-part of application No. 11/305,964, filed on Dec. 19, 2005, which is a continuation-in-part of application No. 10/852,415, filed on May 24, 2004, now Pat. No. 7,403,804, which is a continuation-in-part of application No. 09/832,585, filed on Apr. 11, 2001, now Pat. No. 6,574,490, and a continuation-in-part of application No. 10/281,576, filed on Oct. 28, 2002, now Pat. No. 7,202,091, and a continuation-in-part of application No. 10/378,237, filed on Mar. 3, 2003, now Pat. No. 6,865,408, and a continuation-in-part of application No. 10/753,506, filed on Jan. 8, 2004, now Pat. No. 7,016,713.

(51) Int. Cl.
*G08B 13/14* (2006.01)
(52) U.S. Cl. ............... 340/573.1; 340/576; 600/310
(58) Field of Classification Search ........... 340/573.1, 340/573.4, 573.5, 573.7, 552, 554, 555, 557, 340/567, 576; 600/310, 316, 322, 473; 436/501; 713/186
See application file for complete search history.

(56) References Cited

U.S. PATENT DOCUMENTS

| 4,699,149 | A | * | 10/1987 | Rice ........................... 600/475 |
|---|---|---|---|---|
| 5,348,002 | A | * | 9/1994 | Caro .......................... 600/310 |
| 5,907,407 | A | * | 5/1999 | Atkinson et al. ............. 356/437 |
| 6,040,194 | A | * | 3/2000 | Chick et al. ................. 436/501 |
| 6,067,167 | A | * | 5/2000 | Atkinson et al. ............. 356/437 |
| 6,223,063 | B1 | * | 4/2001 | Chaiken et al. ............. 600/310 |
| 6,512,937 | B2 | * | 1/2003 | Blank et al. ................. 600/322 |
| 6,574,501 | B2 | * | 6/2003 | Lambert et al. ............. 600/473 |
| 7,398,119 | B2 | * | 7/2008 | Lambert et al. ............. 600/473 |
| 2003/0163710 | A1 | * | 8/2003 | Ortiz et al. .................. 713/186 |

* cited by examiner

*Primary Examiner*—Van T. Trieu
(74) *Attorney, Agent, or Firm*—V. Gerald Grafe

(57) ABSTRACT

The present invention relates generally to non-invasive methods and apparatuses for determining analyte properties of a subject and identity characteristics of a subject. Embodiments of the present invention provide analyte property determination and identity determination or verification from the same spectroscopic information, making unauthorized use or misleading results less likely that in systems that include separate analyte and identity determinations. The invention can be used to control and monitor individuals accessing controlled environments.

38 Claims, 22 Drawing Sheets

APPARATUS AND METHOD FOR NONINVASIVELY MONITORING FOR THE PRESENCE OF ALCOHOL OR SUBSTANCES OF ABUSE IN CONTROLLED ENVIRONMENTS

CROSS REFERENCES TO RELATED APPLICATIONS

This application claims priority under 35 U.S.C § 120 as a continuation-in-part of U.S. patent application Ser. No. 11/305,964, entitled "Apparatus and Methods for Mitigating the Effects of Foreign Interferents on Analyte Measurements in Spectroscopy," filed Dec. 19, 2005, which application was a continuation-in-part of U.S. patent application Ser. No. 10/852,415, entitled "Noninvasive determination of alcohol in tissue," filed May 24, 2004, now U.S. Pat. No. 7,403,804, incorporated herein by reference, which application was a continuation-in-part of U.S. patent application Ser. No. 09/832,585, entitled "System For Non-Invasive Measurement Of Glucose In Humans," filed Apr. 11, 2001, now U.S. Pat. No. 6,574,490, and of U.S. patent application Ser. No. 10/281,576, entitled "Optically Similar Reference Samples", filed Oct. 28, 2002, now U.S. Pat. No. 7,202,091, and of U.S. patent application Ser. No. 10/378,237, entitled "System For Non-Invasive Measurement Of Glucose In Humans," filed Mar. 3, 2003, now U.S. Pat. No. 6,865,408, and of U.S. patent application Ser. No. 10/753,506, "Noninvasive Determination of Direction and Rate of Change of an Analyte," filed Jan. 8, 2004, now U.S. Pat. No. 7,016,713, each of which is incorporated herein by reference.

TECHNICAL FIELD

The present invention relates to noninvasive monitoring for the presence or concentration of alcohol or other substances in individuals in probation/corrections, alcohol treatment centers, and restricted access environments, and more specifically to spectroscopic methods and apparatuses for detecting the presence or concentration of alcohol or substances of abuse in individuals in any of a variety of controlled environments.

BACKGROUND OF THE INVENTION

Alcohol abuse is a national problem that extends into virtually all aspects of society.

Spectroscopic measurements, such as those described by Robinson in U.S. Pat. No. 6,278,889 for glucose measurements, offer promise for completely noninvasive alcohol measurements in people. In U.S. Pat. No. 5,743,349, titled "Non-invasive optical blood alcohol concentration reader and vehicle ignition interlock system and method", filed Sep. 23, 1996, since abandoned, Steinberg discloses a vehicle ignition interlock that incorporates a spectroscopic means for noninvasively measuring blood alcohol concentration. Steinberg does not disclose any means for verifying the identity of the tested individual.

Furthermore, Steinberg discloses the measurement of electromagnetic radiation in the 250 to 3000 nm wavelength range by introducing radiation to a finger and measuring the light exiting the opposite side of the finger. Such transmission approaches, while potentially feasible in the visible region (400 to 800 nm), are limited by the strong absorption of water (water is a major component of the tissue) in the near and mid-infrared regions (>800). For tissue samples greater than a few millimeters in thickness, the absorption of water results in virtually no measurable radiation exiting the opposite side of the sample. Consequently, little if any radiation remains for subsequent measurement of alcohol concentration.

In U.S. Pat. No. 6,229,908, titled "Driver Alcohol Ignition Interlock", filed Apr. 22, 1997, Edmonds and Hopta disclose an ignition interlock incorporating a spectroscopic alcohol measurement of the finger combined with a means for generating a finger print image. The finger print image is intended to identify the operator in order to ensure that the alcohol measurement was acquired from the prospective driver and not a passenger. Similar to existing breath-based interlocks, the finger print image is obtained from a measurement that is distinct from the spectroscopic measurement, thereby yielding potential for circumventing the interlock. Further, the method disclosed in 6,229,908 relies on automated fingerprint reading, a technology which has demonstrated performance shortcomings.

SUMMARY OF THE INVENTION

The present invention provides an effective apparatus and method for monitoring for the presence or concentration of alcohol or substances of abuse in controlled environments, and is considered in terms of three primary components. FIG. 1 is a schematic illustration of an embodiment of such an apparatus. A first component is a system 1 that can measure the presence or concentration of alcohol or substance of abuse in an individual. A second component 2 is a system that can verify or determine that the measurement was obtained from a specific individual or a member of a specific group of individuals. A third component 3 is a system that performs an action based upon the alcohol or substance of abuse measurement and identity verification/determination results, where the action can be dependent on and vary according to the specific environment under consideration. For example, when alcohol is detected in an individual housed in a residential treatment center, the action performed by the present invention can be documentation of the positive alcohol test followed by notification of a facility administrator. In other embodiments, such as those intended to control access to secure facilities, the present invention can deny entry to any individual that either failed the alcohol/substance of abuse measurement or was determined to be unauthorized to enter by the identity verification or determination measurement. The present invention links the first two components of the disclosed apparatuses and methods via a single spectroscopic measurement, which significantly reduces methods for circumvention. For demonstrative purposes the discussion herein generally refers to infrared and near-infrared spectroscopic measurements; visible (UV-vis), Raman, and fluorescence spectroscopic measurements are also feasible techniques for the present invention.

Absorption spectroscopy is a generally known analytical method. In some forms, absorption spectroscopy measures the electromagnetic radiation (typical wavelength range of 0.3-25 µm) that a substance absorbs at various wavelengths, though other methods measure other effects a substance has on incident light. Absorption phenomena can be related to molecular vibrations and shifts in energy levels of individual atoms or electrons within a molecule. These phenomena cause the absorbing molecule or atom to switch to a higher energy state. Absorption occurs most frequently in limited ranges of wavelengths that are based upon the molecular structure of the species present in the measured sample. Thus, for light passing through a substance at several wavelengths, the substance will absorb a greater percentage of photons at certain wavelengths than it will at others.

At the molecular level, many primary vibrational transitions occur in the mid-infrared wavelength region (i.e., wavelengths between 2.5-6 µm). However, for some measurements, use of the mid-infrared region can be problematic because molecules with strong absorbance properties (e.g. water) can result in the total absorption of virtually all light introduced to the sample being measured. The problem can often be overcome through the use of shorter wavelengths (typically in the near infrared region of 0.7-2.5 µm) where weaker overtones and combinations of the mid-infrared vibrations exist. Thus, the near-infrared region can be employed in such situations as it preserves the qualitative and quantitative properties of mid-infrared measurements while helping to alleviate the problem of total light absorption.

As mentioned above, alcohol and other analytes absorb light at multiple wavelengths in both the mid- and near-infrared range. Due to the overlapping nature of these absorption bands, reliable analyte measurements can be very difficult if only a single wavelength were used for analysis. Thus, analysis of spectral data can incorporate absorption characteristics at several wavelengths, which enables sensitive and selective measurements of the desired attributes. In multi-wavelength spectroscopy, multivariate analysis techniques can be used to empirically determine the relationship between measured spectra and a property of interest (e.g. analyte concentration).

Advances in optical materials and multivariate algorithms over the last several decades have created the potential for expanding spectroscopic measurements into new areas of interest. One such area is noninvasive measurements of analytes in skin. Human skin, as depicted in FIG. 2, is a multi-layer system comprised of the epidermis, dermis, and subcutaneous layers. Each layer has different physiological and chemical characteristics that influence its relative contribution to spectroscopic measurements of tissue. For example, the subcutaneous layer is largely comprised of lipids that are typically absent in other tissue layers. In contrast, the dermal layer is composed primarily of water and collagen. As a result, spectroscopic measurements of the present invention inherently contain contributions of the analytes within each tissue layer and therefore can provide insight into both the chemical composition and the structure of the tissue.

In many cases the complexity of the spectroscopic tissue measurements requires application of multivariate models to elucidate the property of interest (e.g. alcohol concentration or biometric identification/verification). In some applications, such as the apparatuses and methods of the present invention, the inherent spectral complexity can be advantageous. Due to natural physiological variation in skin, people have different tissue properties (e.g. dermal hydration, collagen densities, and tissue layer thicknesses). A spectroscopic measurement can capture the inter-subject differences, which enables discrimination between individuals. In other words, the noninvasive spectroscopic signal of the present invention simultaneously enables both analyte (alcohol or substances of abuse) and biometric measurements thereby providing and integrally linking two of the three components of an effective method or apparatus for monitoring for the presence or concentration of alcohol or a substance of abuse in a controlled environment.

The third component of the embodiments of the present invention is a system that combines the analyte and identity verification measurements, stores the results, and performs an action based upon the results. For example, when alcohol is detected in an individual housed in a residential treatment center, the action performed by the present invention can include documentation of the positive alcohol test and notification of a facility administrator. In other embodiments, such as those intended to control access to secure facilities, the present invention can deny entry to any individual that either failed the alcohol/substance of abuse measurement or was determined to be unauthorized to enter by the identity measurement.

The advantages and features of novelty that characterize the present invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter in which there are illustrated and described preferred embodiments of the present invention.

DETAILED DESCRIPTION OF THE INVENTION

Figure 1:
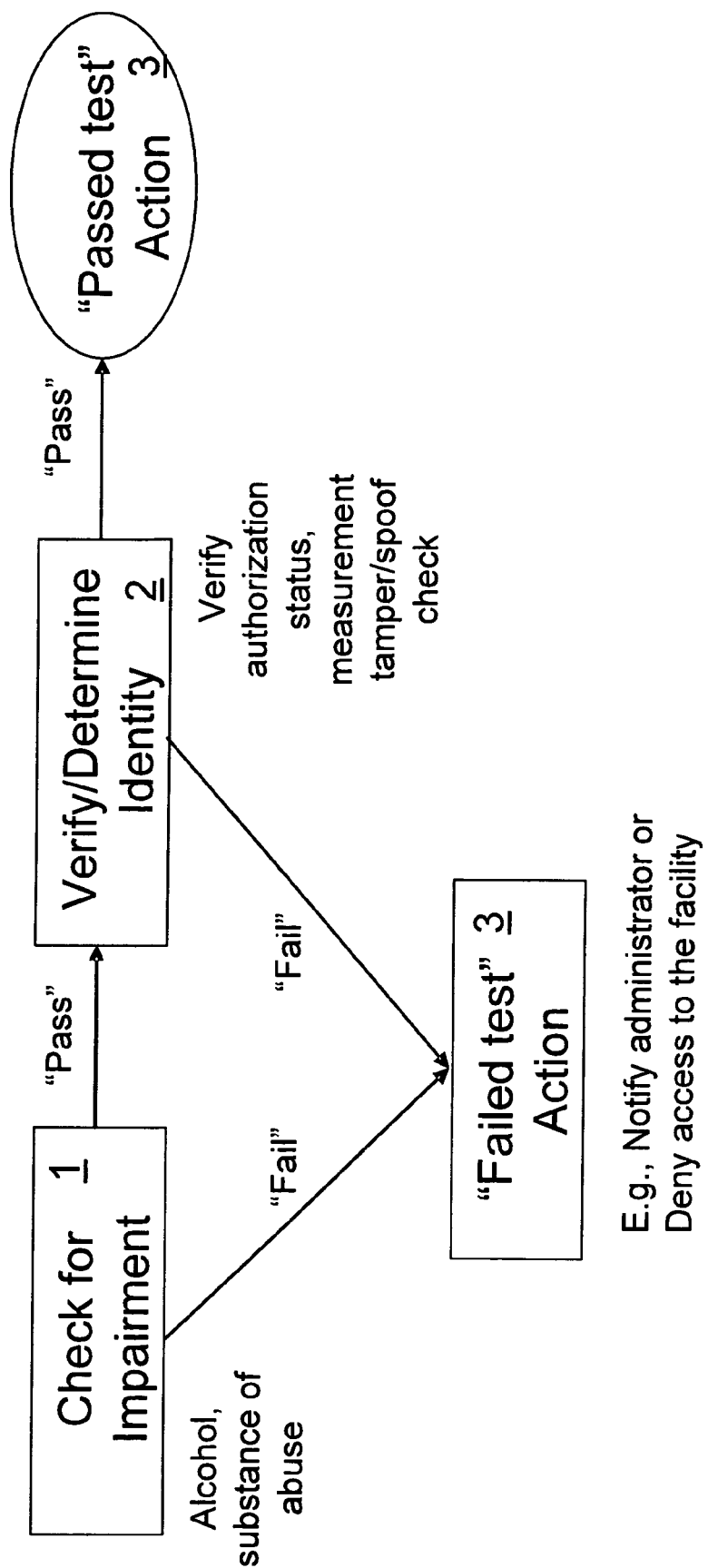
FIG. 1 is a schematic illustration of an embodiment of the present invention.

In U.S. patent application Ser. No. 10/852,415, entitled "Noninvasive determination of alcohol in tissue," filed May 24, 2004 and incorporated herein by reference, Ridder et al. disclose a method for the noninvasive measurement of alcohol based on spectroscopic techniques that provides an alternative to the current blood, breath, urine, saliva, and transdermal methods. The device requires passive contact between the noninvasive device and a tissue surface such as a finger, forearm, palm, or earlobe in order to measure the alcohol concentration in the tissue. The alcohol measurement described in Ridder typically requires only a short period of time (i.e. 1 minute) and thus is suitable for use the environments disclosed in the present invention.

In U.S. Pat. No. 6,628,809, titled "Apparatus and method for identification of individuals by near-infrared spectrum", and in U.S. Pat. No. 6,560,352, titled "Apparatus and method of biometric identification or verification of individuals using optical spectroscopy", both incorporated herein by reference, Rowe et. al. disclose spectroscopic methods for determining the identity or verifying the identity of an individual using spectroscopic measurements of tissue. Such spectroscopic methods provide an alternative to existing fingerprint, voice recognition, video recognition, and bodily feature identification for the controlled environments contemplated with the present invention.

An advantage of the present invention is that the spectroscopic signal used to measure alcohol concentration, such as that described in Ser. No. 10/852,415, also contains chemical and structural biometric information of the individual being measured as discussed in U.S. Pat. No. 6,628,809 and U.S. Pat. No. 6,560,352. As the spectroscopic signal inherently contains both alcohol and biometric information, the two measurements are integrally linked, which results in a more robust measurement that is not susceptible to many circumvention approaches. The spectroscopic measurement of analytes can also be combined with other identification approaches (e.g., to produce a system that identifies an individual and indicates the presence or concentration of alcohol or a substance of abuse), and with other systems alone (e.g., to prevent admission of any intoxicated or drug-using person to a facility regardless of identity) or with identification (e.g., to limit facility admission to authorized individuals who are not intoxicated).

Another aspect of the present invention is the ability to incorporate the measurement of analytes other than alcohol into the measurement system. For example, spectroscopic methods, such as those described by Miller et. al. in "Minimally invasive spectroscopic system for intraocular drug detection", Journal of Biomedical Optics 7 (1), 27-33, have been applied to the detection and quantification of substances of abuse. As such the noninvasive spectroscopic measurement described in Ridder will contain the spectroscopic signals of substances of abuse if present within the measured tissue. From the perspective of the present invention, methods based upon the combination of noninvasive spectroscopic measurements of alcohol or substances of abuse with an explicitly linked spectroscopic biometric measurement represent a significant advantage relative to existing approaches.

Detailed embodiments of the present invention are disclosed herein. However, it is to be understood that the disclosed embodiments are merely exemplary of the present invention that can be embodied in various systems. Therefore, specific details disclosed herein are not to be interpreted as limiting, but rather as a basis for the claims and as a representative basis for teaching one of skill in the art to variously practice the invention.

For the purposes of this invention, the term "analyte concentration" generally refers to the concentration of an analyte such as alcohol. The term "analyte property" includes analyte concentration and other properties, such as the presence or absence of the analyte or the direction or rate of change of the analyte concentration, which can be measured in conjunction with or instead of the analyte concentration. While the term "analyte" generally refers to alcohol, other chemicals, particularly substances of abuse and alcohol byproducts, can also be determined with the present invention. For the purposes of this invention, the term "alcohol byproducts" includes the adducts and byproducts of the metabolism of alcohol by the body including, but not limited to, acetone, acetaldehyde, and acetic acid. The term "substances of abuse" refers to, but is not limited to, THC (Tetrahydrocannabinol or marijuana), cocaine, M-AMP (methamphetamine), OPI (morphine and heroin), OxyContin, Oxycodone, and PCP (phencyclidine). The present invention addresses the need for analyte measurements of samples utilizing spectroscopy where the term "sample" generally refers to biological tissue. The term "subject" generally refers to a person from whom a sample measurement was acquired. The term "controlled environments" refers to any environment where the presence of an individual is subject to any restrictions related to alcohol, substances of abuse, or identity. This includes, but is not limited to, business offices, government buildings, probation centers, locations where individuals are located under home arrest, community corrections facilities, alcohol and substance of abuse treatment centers, public places incorporating check-in kiosks, and facilities or equipment with restricted access such as nuclear power plants and weapons storage facilities.

For the purposes of this invention the term "dispersive spectrometer" indicates a spectrometer based upon any device, component, or group of components that spatially separate one or more wavelengths of light from other wavelengths. Examples include, but are not limited to, spectrometers that use one or more diffraction gratings, prisms, or holographic gratings. For the purposes of this invention the term "interferometric/modulating spectrometer" indicates a class of spectrometers based upon any device, component, or group of components that either modulate different wavelengths of light to different frequencies in time or selectively transmits or reflects certain wavelengths of light based upon the properties of light interference. Examples include, but are not limited to, Fourier transform interferometers, Hadamard spectrometers, Sagnac interferometers, mock interferometers, Michelson interferometers, one or more etelons, acousto-optical tunable filters (AOTF's), and one or more LEDs or VCSELs that are scanned or modulated. One skilled in the art recognizes that spectrometers based on combinations of dispersive and interferometric/modulating properties, such as those based on lamellar gratings, are also suitable for the present invention.

The invention makes use of signals, described in some of the examples as absorbance or other spectroscopic measurements. Signals can comprise any measurement obtained concerning the spectroscopic measurement of a sample or change in a sample, e.g., absorbance, reflectance, intensity of light returned, fluorescence, transmission, Raman spectra, or various combinations of measurements, at one or more wavelengths. Some embodiments make use of one or more models, where such a model can be anything that relates a signal to the desired property. Some examples of models include those derived from multivariate analysis methods such as partial least squares regression (PLS), linear regression, multiple linear regression (MLR), classical least squares regression (CLS), neural networks, discriminant analysis, principal components analysis (PCA), principal components regression (PCR), cluster analysis, and K-nearest neighbors. Single or multi-wavelength models based on the Beer-Lambert law are special cases of classical least squares and are thus included in the term multivariate analysis for the purposes of the present invention.

The following detailed description should be read with reference to the drawings. The drawings, which are not necessarily to scale, depict illustrative embodiments that are not intended to limit the scope of the invention. For the purposes of the application, the term "about" applies to all numeric values, whether or not explicitly indicated. The term "about" generally refers to a range of numbers that one of skill in the art would consider equivalent to the recited value (i.e., having the same function or result). In some instances, the term "about" can include numbers that are rounded to the nearest significant figure.

As mentioned above, an effective apparatus or method for monitoring for the presence or concentration of alcohol or substances of abuse in controlled environments can be considered in terms of three primary components. The first component is a system that can measure the presence or concentration of an analyte (alcohol or substance of abuse) in an individual. The second component is a system that can verify that the measurement was obtained from a specific individual or member of a specific group of individuals. The third component is a system that combines the analyte and identity verification measurements, stores the results, and performs an action based upon the results where said action can be dependent on and vary according to the specific environment under consideration. For example, when alcohol is detected in an individual housed in a residential treatment center, the action performed by the present invention can be documentation of the positive alcohol test and notification of a facility administrator. In other embodiments, such as those intended to control access to secure facilities, the present invention can deny entry to any individual that either failed the alcohol/ substance of abuse measurement or was determined to be unauthorized to enter by the identity verification measurement. The present invention links the first two components of the disclosed apparatuses and methods via a single spectroscopic measurement, which significantly reduces methods for circumvention.

Background of Tissue and Origins of the Spectroscopic Signal

Figure 2:
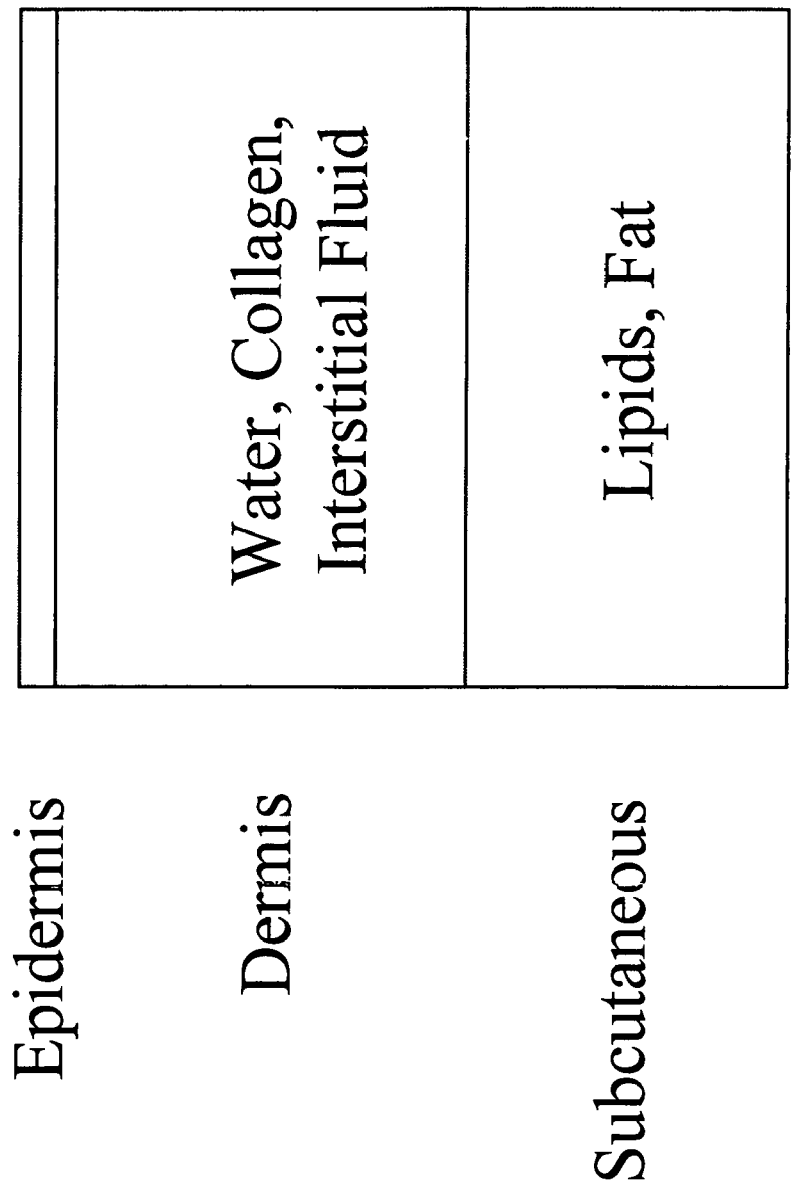
FIG. 2 is a diagram of the layered structure of human skin.

Human skin (FIG. 2) is comprised of epidermal, dermal, and subcutaneous layers, each of which has different physiological and chemical characteristics that influence their relative utility for alcohol measurements. The epidermis contains very little extracellular fluid, and therefore contains minimal information about hydrophilic analytes such as alcohol. The subcutaneous layer is largely comprised of lipids that have low water (and alcohol) solubility which make it poorly suited to alcohol measurements. However, the dermal layer has high water content (generally around 65%) and an extensive capillary bed conducive to the transport of alcohol, which makes it a useful layer of skin tissue for alcohol (or any analyte with high water solubility) measurements. The relative utility of the layers can depend upon the analyte property of interest. For example, THC is strongly soluble in lipids, which can increase the importance of the subcutaneous layer in THC measurements relative to its importance in alcohol measurements.

The layered structure of the tissue provides a wealth of spectroscopic information that can be used to discriminate between people. This biometric signal is a function of many skin properties such as the relative thicknesses of the tissue layers, their scattering coefficients, and the analyte concentrations within each layer. For example, the subcutaneous layer is largely comprised of lipids that are typically absent in other tissue layers. In contrast, the dermal layer is composed primarily of water and collagen. As a result, the spectroscopic measurement contains the relative signal contributions of these analytes and therefore provides insight into both the chemical composition and structure of the tissue. Because different people have different tissue properties (dermal hydration, collagen densities, tissue layer thicknesses), the spectroscopic measurement simultaneously captures both analyte signals (e.g. alcohol signal) and the inter-subject differences that collectively form the biometric signal.

Figure 3:
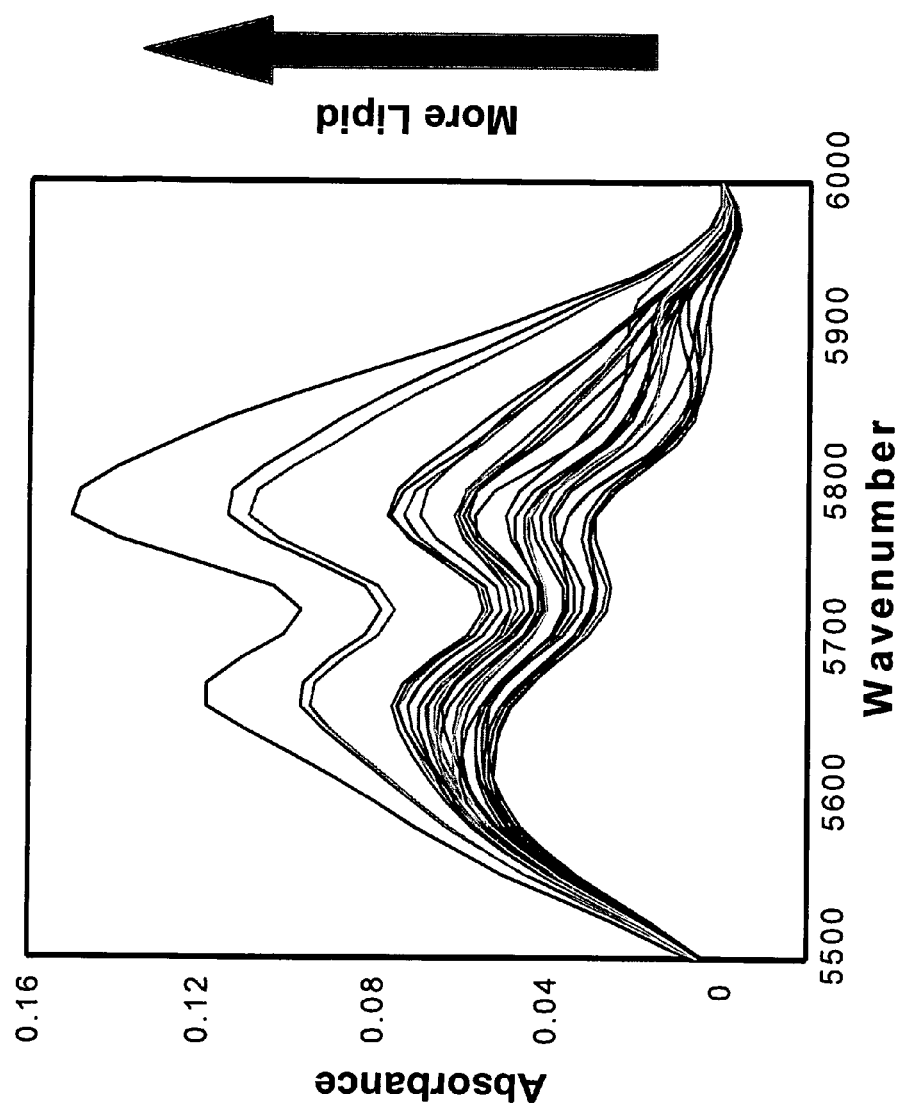
FIG. 3 shows the lipid signals obtained from spectroscopic measurements of 31 individuals.
Figure 4:
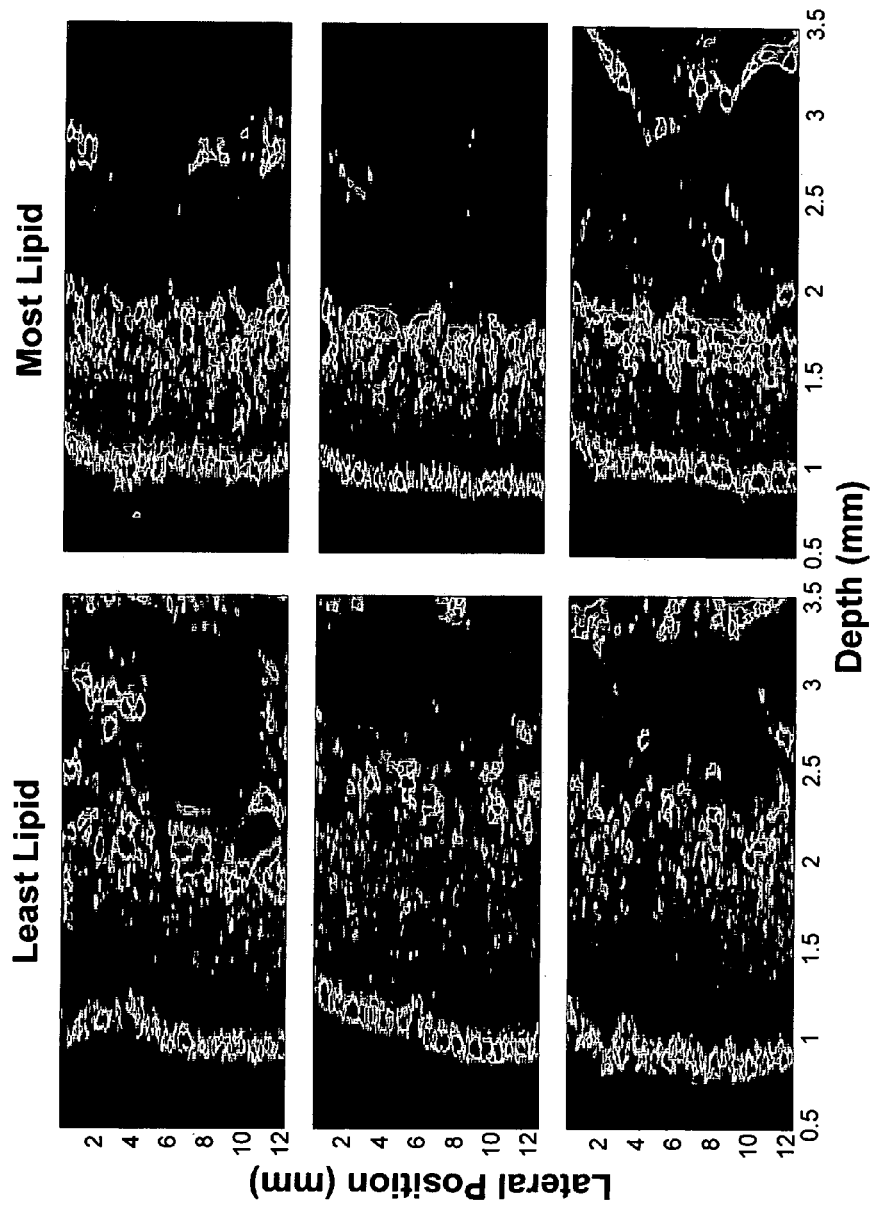
FIG. 4 shows ultrasound images of 6 individuals that demonstrate the difference in tissue structure between people.

FIGS. 3 and 4 combine to provide an example of the inter-subject discriminatory power of the spectroscopic signal. FIG. 3 shows the 5500-6000 $cm^{-1}$ region of NIR spectra obtained from 31 subjects. The pronounced peaks at 5675 and 5800 $cm^{-1}$ correspond to the spectral signature of lipids, which is an indicator that a portion of the NIR signal originated in the subcutaneous tissue layer for some of the 31 subjects. The variation of the lipid signature suggests that the subjects with weaker lipid signal have thicker epidermal and dermal tissue layers, thus preventing the NIR light from reaching the deeper subcutaneous layer where lipids are located. FIG. 4 offers a different perspective that shows ultrasound images that were obtained from 3 of the 31 subjects who exhibited a strong lipid signal and 3 subjects of the 31 that exhibited no discernable lipid signal. In ultrasound images of tissue, a large signal (brighter parts of the image) generally corresponds to a boundary between layers. As such, the strong signal near 1 mm of depth in each window of FIG. 3 corresponds to the ultrasound probe-epidermal interface. The next region of interest is the dermal-subcutaneous boundary, which generally occurs between 1.5 mm and 2.5 mm of depth. Comparison of the two groups demonstrates a marked difference in dermal thickness between the strong and weak lipid signal subjects. Consequently, the magnitude of the lipid signal is of interest because it provides chemical and structural information that can be used to differentiate subjects.

Figure 5:
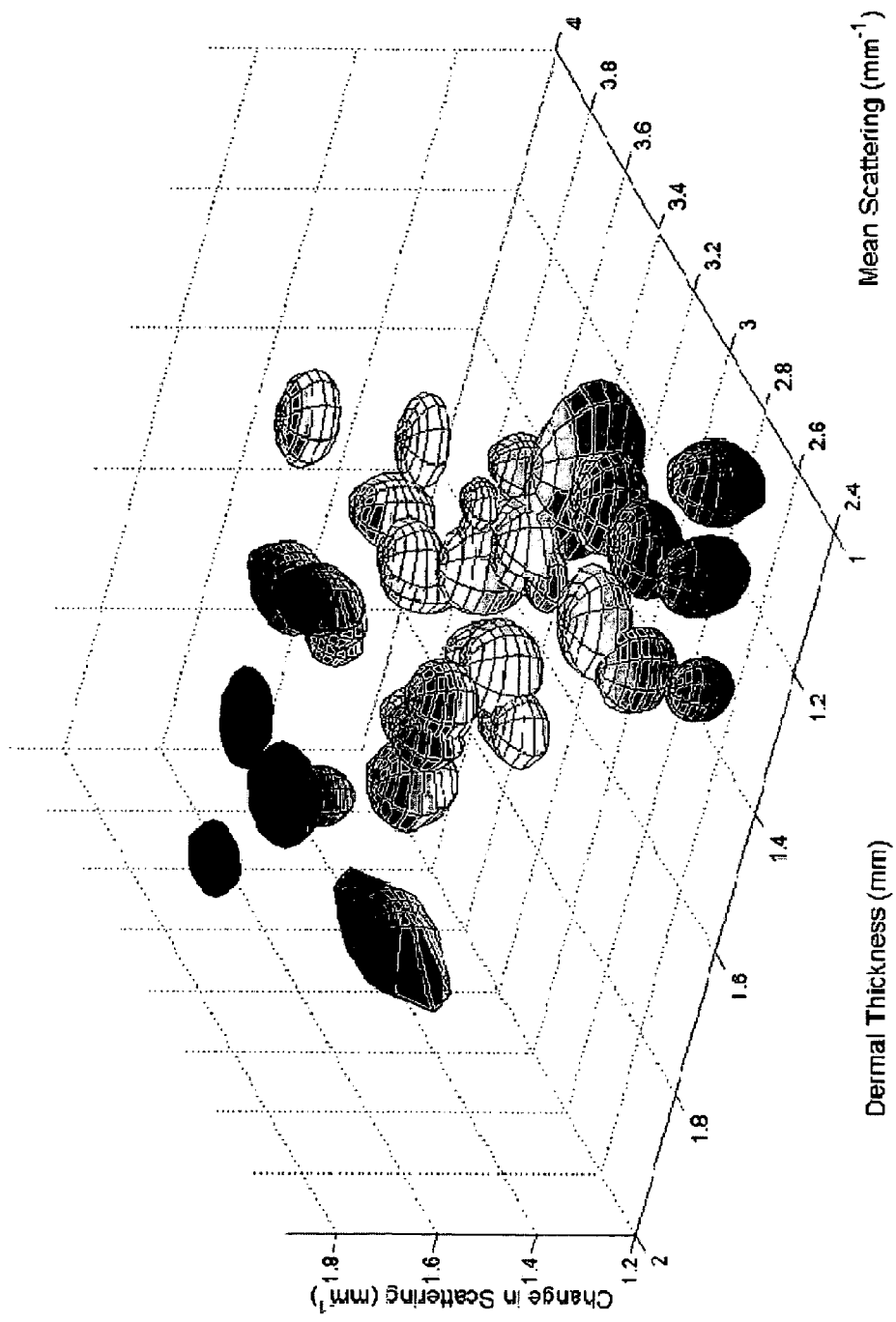
FIG. 5 is a diagram showing the inter-subject discriminatory power of the spectroscopic measurement of the present invention.

While lipid content provides an intuitive example of a discernable property in the spectroscopic measurement, multiple structural and chemical properties can be extracted. In aggregate, these properties form a powerful technique to discriminate between people. FIG. 5 is a visual presentation of the inter-subject resolving power of the measurement using 3 extracted properties. Each ellipsoid in FIG. 5 encompasses the properties extracted from multiple measurements (typically 10-15) obtained from a single subject. Even with only three properties, the measurements acquired from each subject reside in a distinct region of the 3-dimensional space. This example can be extended to include additional properties and thereby further improve the discriminatory power of the biometric signal. The extracted properties can be representative of physical variables (e.g. dermal thickness or scattering coefficient) or mathematically derived from subject measurements (e.g. factors from a principal components analysis, PCA).

The present invention obtains the first two components of the disclosed apparatuses and methods from a single spectroscopic measurement of tissue (e.g., skin). Some demonstrative embodiments of suitable spectroscopic measurement devices are described below. These examples should not be construed as limiting to the invention as one skilled in the art recognizes that other embodiments exist that serve substantially the same function. For example, while the majority of the disclosure relates to near infrared spectroscopic measurements, Raman measurements (and therefore Raman spectrometers) can also be suitable for the present invention.

Embodiments for Measuring the Spectroscopic Signal

Figure 6:
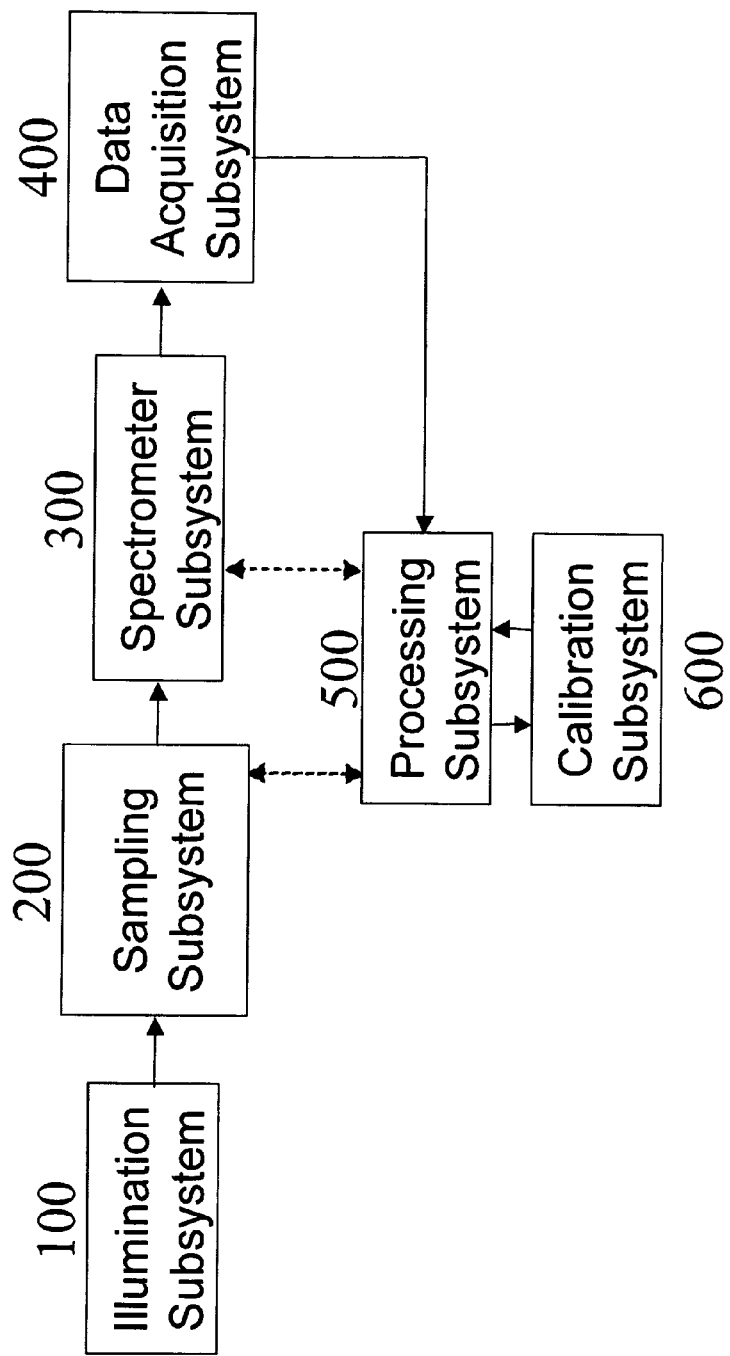
FIG. 6 is a schematic depiction of a system according to the present invention.
Figure 7:
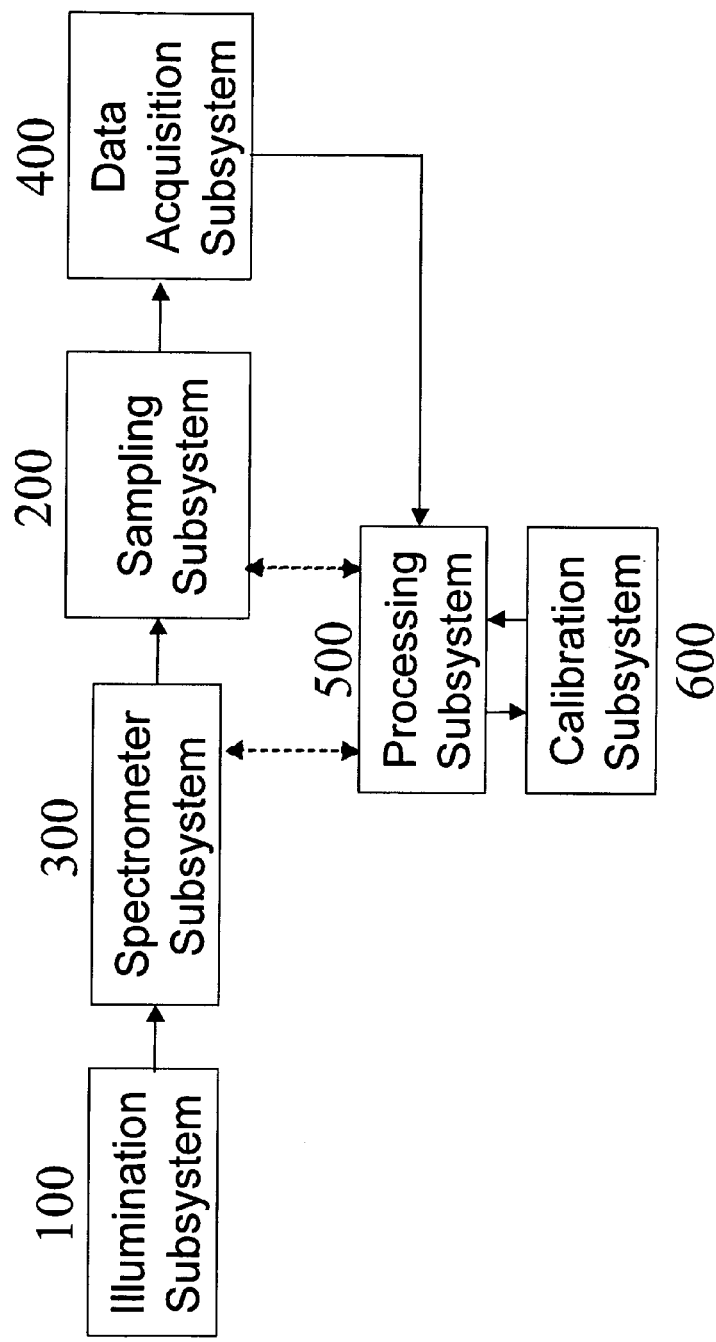
FIG. 7 is a schematic depiction of a system according to the present invention.

Several embodiments of the present invention include an apparatus for measuring the spectroscopic signal of tissue, typically skin. As an example of such an apparatus, FIG. 6 shows a schematic depiction of a non-invasive measurement device suitable for use with the present invention. The overall system can be viewed for discussion purposes as comprising six subsystems; those skilled in the art will appreciate other subdivisions of the functionality disclosed. The subsystems include an illumination subsystem 100, a sampling subsystem 200, a spectrometer subsystem 300, a data acquisition subsystem 400, a processing subsystem 500, and a calibration subsystem 600. The subsystems can be designed and integrated in order to achieve a desirable signal-to-noise ratio and performance. FIG. 7 is a schematic depiction of an alternative arrangement of the elements shown in FIG. 6: the spectrometer subsystem and sampling subsystem have been exchanged relative to the system of FIG. 6. Those skilled in the art will appreciate the effect of interchanging elements and subsystems in an optical path. The subsequent discussion assumes the arrangement of FIG. 6 for simplicity, but is not meant to preclude alternative arrangements of the subsystems.

In some embodiments of the present invention, the illumination subsystem 100 generates near-infrared (NIR) light to interrogate the skin tissue. In an exemplary embodiment, the illumination subsystem contains a broadband, polychromatic light source that emits radiation in the NIR portion of the spectrum. The light source can also emit radiation outside of the NIR. An example of a suitable light source is a tungsten filament lamp. Another example light source is a resistive element such as those commonly used as igniters for furnaces and stoves. These light sources have a lower color temperature than standard filament lamps and are therefore more efficient in the near-infrared spectral region. These sources also have comparatively large emissive surfaces that are less sensitive to spatial effects that are encountered throughout the lifetime of the light source. An additional advantage of igniter-based light sources is a substantially longer lifetime when compared to filament lamps.

Polychromatic sources can also be generated by combining multiple monochromatic or narrow band sources. For example, multiple light-emitting diodes (LED's) and/or vertical cavity surface emitting lasers (VCSEL's) can be combined to form a polychromatic light source. Various optical methods can be used to combine the outputs of the various individual light sources into a single beam. Such methods include, but are not limited to, reflective integrating chambers, diffuse integrating chambers, a light homogenizer or light pipe, and optical fibers. The output intensities of the discrete light sources can also be independently modulated at predetermined frequencies.

In some embodiments, such as those employing Raman spectroscopy, a monochromatic source is used. Solid state or gas lasers are suitable light sources in these embodiments. Some examples lasers include but are not limited to diode, vertical cavity surface emitting lasers (VCSEL's), NdYg, and HeNe lasers. Polychromatic light sources are also feasible if they are sufficiently narrowed using optical filters. Other illumination systems that can be suitable with embodiments of the present invention are described by Johnson in U.S. Pat. No. 6,862,091, issued Mar. 1, 2005, by Ridder in U.S. Pat. No. 6,684,099, issued Jan. 27, 2004, and by Maynard in U.S. Pat. No. 6,654,125, issued Nov. 25, 2003, each of which is incorporated herein by reference.

Figure 8:
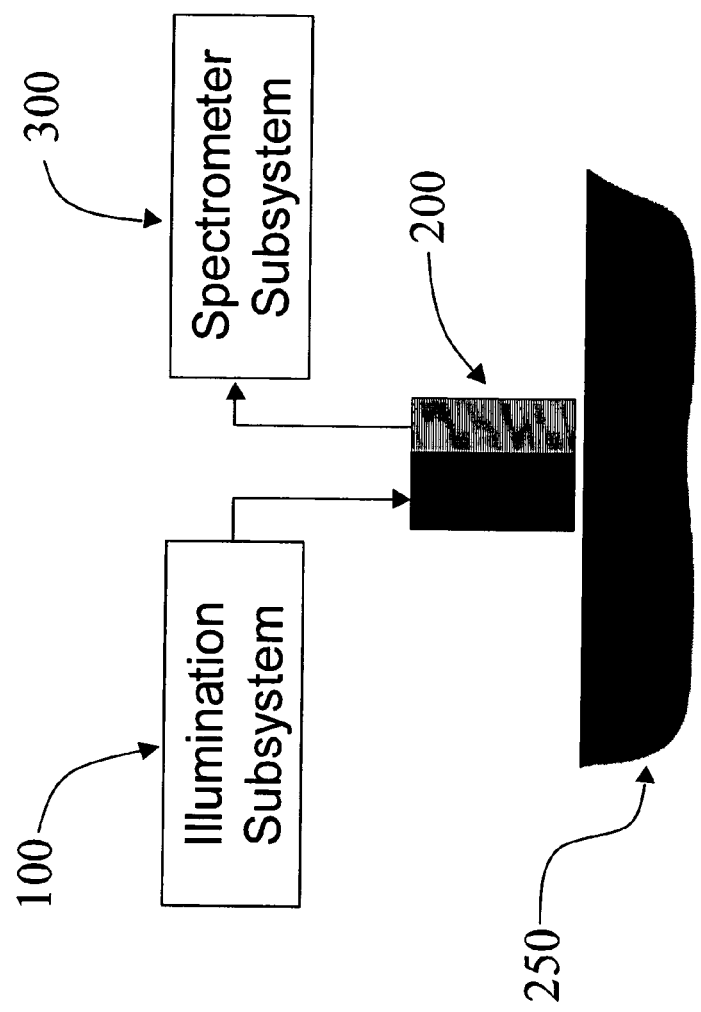
FIG. 8 is a schematic depiction of a system that measures a sample in reflectance.
Figure 9:
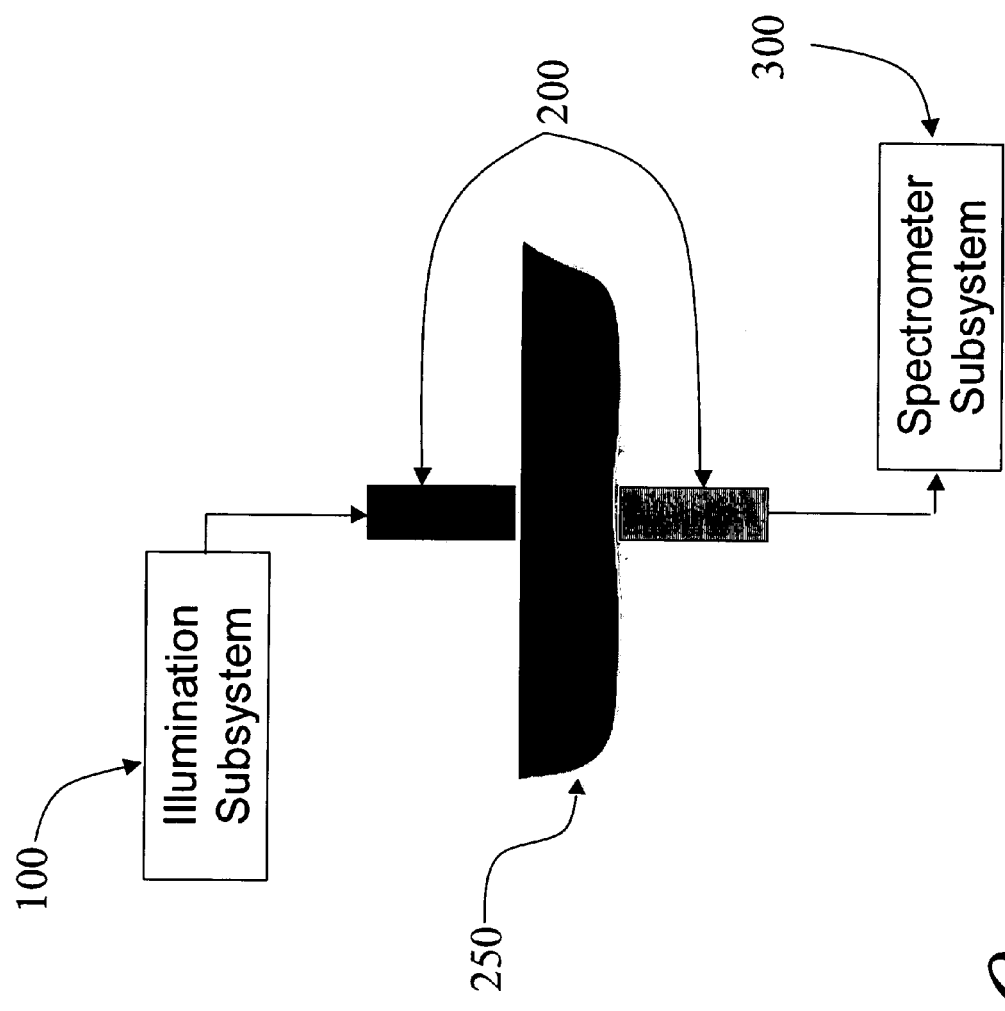
FIG. 9 is a schematic depiction of a system that measures a sample in transmission.

In practicing the method of the present invention, an area of the sample can be selected as the point of analysis for the sampling subsystem 200. In the case of noninvasive tissue measurements, this area can include the finger, palms, wrists, earlobe, forearms or any other skin surface. Further, even in the case of using fingers, the present invention allows use of multiple sites along the area. For example, the finger can be measured on both the dorsal and ventral surfaces. Embodiments of the sampling subsystem 200 can be such that light is introduced and collected from the sample 250 in either reflectance or transmission geometries (shown in FIGS. 8 and 9, respectively). A preferred embodiment of the sampling subsystem 200 measures the underside of the forearm using reflectance geometry, and will be used to describe various embodiments of the present invention.

Another advantage of the present invention is that it, unlike fingerprint readers, can use different fingers (or other sites) for enrollment and for subsequent verification. This capability provides for increased enrollment efficiency since the user only has to present one enrollment site to the system, but also provides critical flexibility during the use of the device. An example of this flexibility is the case where the user has enrolled a site on a particular hand and that particular site is unavailable for subsequent analysis due to some injury or other contamination of the site. This spectroscopic-based biometric system of the present invention can operate on the site from the other hand without previous enrollment of such site.

Figure 10:
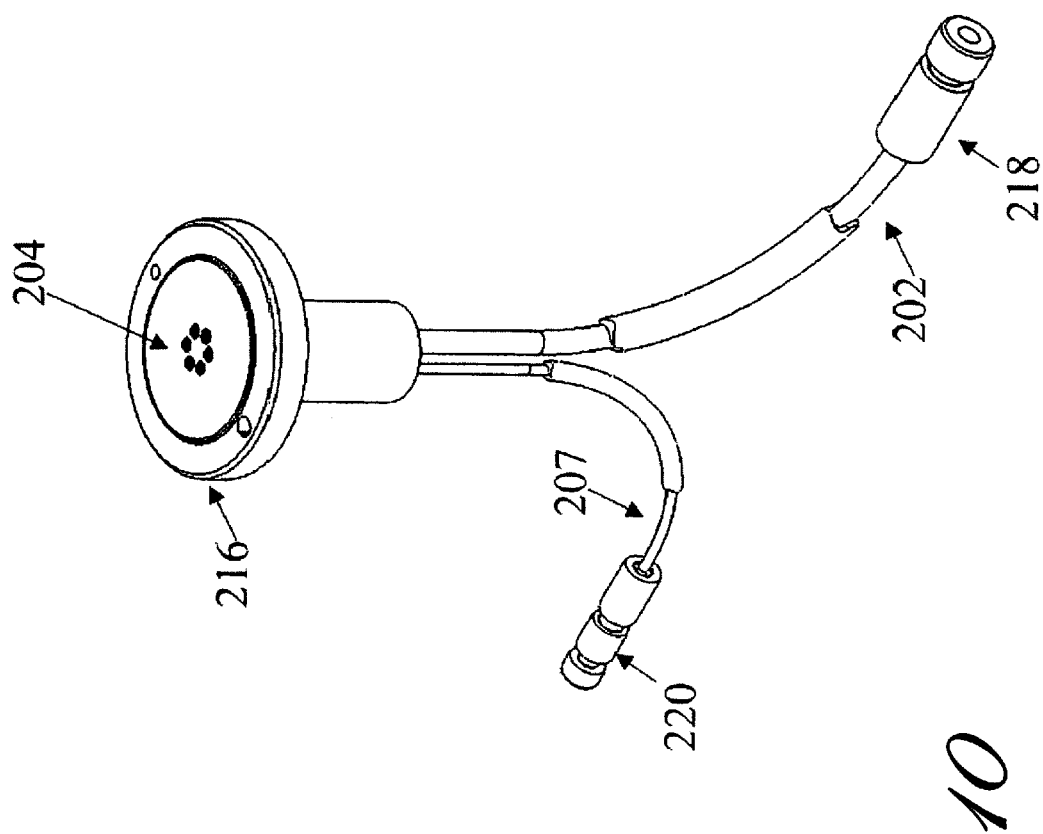
FIG. 10 is a perspective view of elements of an example tissue sampling subsystem.

As illustrated in FIG. 6, the sampling subsystem 200 introduces radiation generated by the illumination subsystem 100 to the sample and collects portions of the radiation that were not absorbed by the sample and sends that radiation to a spectrometer subsystem 300 for measurement. FIGS. 10 through 14 depict elements of preferred embodiments of the sampling subsystem 200. Referring to FIG. 10, the sampling subsystem 200 has an optical input 202, a sampling surface 204 which forms an interface 206 that interrogates the sample and an optical output 207. In a preferred subsystem, a device that thermostats the sampling subsystem/sample interface is included. In other embodiments, an index matching fluid can be used to improve the optical interface between the sample and sampling subsystem. See, e.g. U.S. Pat. No. 6,152,876 to Robinson et al., incorporated herein by reference. In some measurement applications, the index matching fluid can be considered an interferent that warrants application of a mitigation method as described in co-pending U.S. application Ser. No. 11/305,964, incorporated herein by reference.

Figure 11:
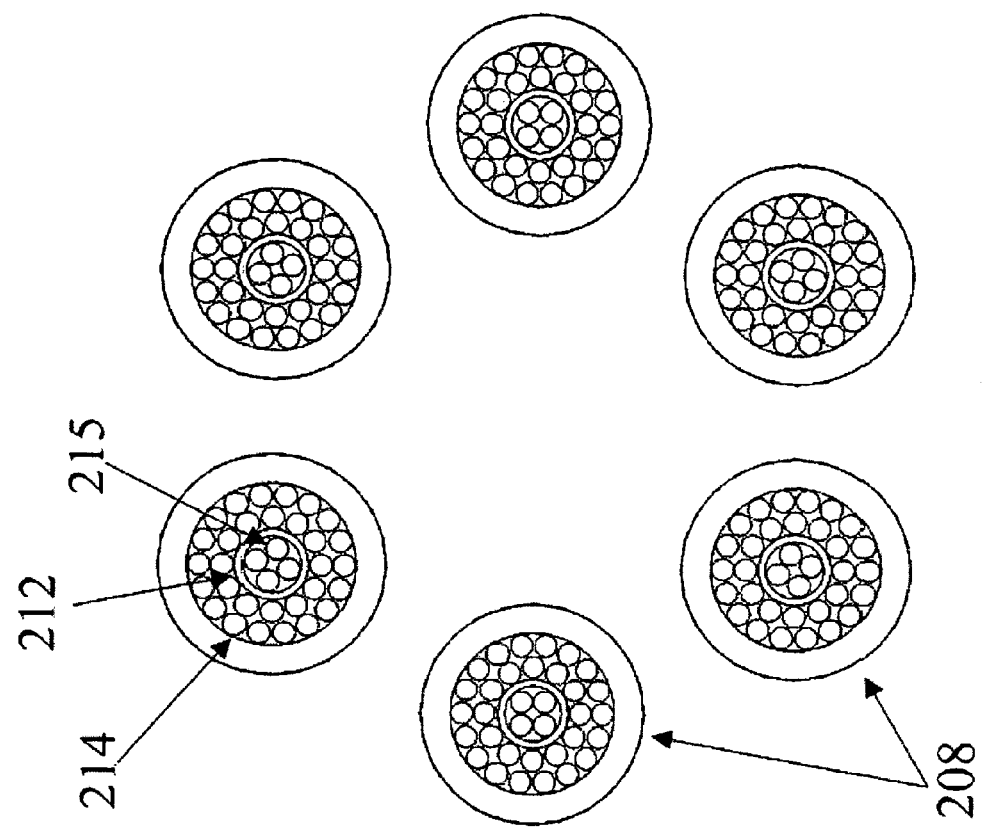
FIG. 11 is a plan view of the sampling surface of the tissue sampling subsystem, showing an example arrangement of input and output optical fiber ends.

The optical input 202 of the sampling subsystem 200 receives radiation from the illumination subsystem 100 (e.g., light exiting a light pipe or other means for coupling light) and transfers that radiation to the interface 206. As an example, the optical input can comprise a bundle of optical fibers that are arranged in a geometric pattern that collects an appropriate amount of light from the illumination subsystem. The sampling head 216 includes a sampling surface 204, polished flat to encourage formation of a good interface with the sample and prevent accumulation of interferents on the sampling head surface. FIG. 11 depicts one example arrangement. The plan view depicts the ends of the input and output fibers in a geometry at the sampling surface including six clusters 208 arranged in a circular pattern. Each cluster includes four central output fibers 212, which collect diffusely reflected light from the sample. Around each grouping of four central output fibers 212 is a cylinder of material 215, which ensures about a 100 μm gap between the edges of the central output fibers 212 and the inner ring of input fibers 214. The 100 μm gap can be important to measuring certain analytes. As shown in FIG. 11, two concentric rings of input fibers 214 can be arranged around the cylinder of material 215. As shown in one example embodiment, 32 input fibers surround four output fibers.

Figure 12:
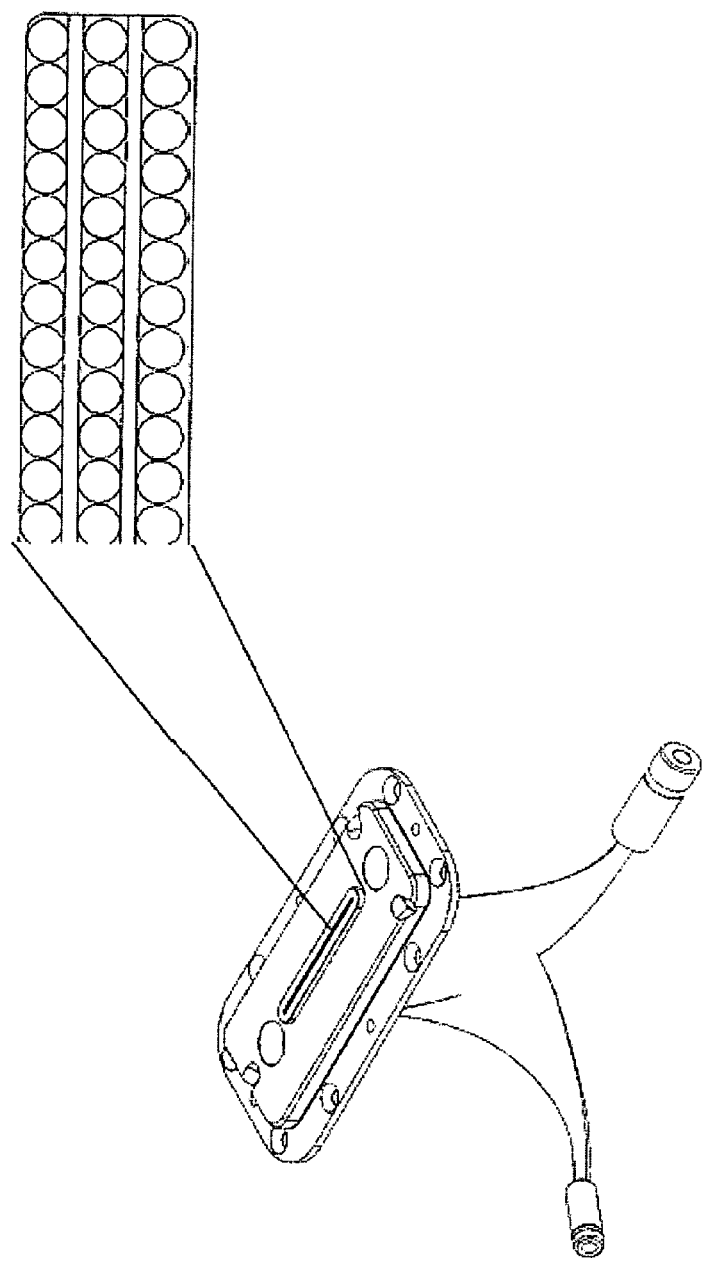
FIG. 12 is an alternative embodiment of a sampling surface of a tissue sampling subsystem.

FIG. 12 demonstrates an alternative to cluster geometries for the sampling subsystem. In this embodiment, the illumination and collection fiber optics are arranged in a linear geometry. Each row can be either for illumination or light collection and can be of any length suitable to achieve sufficient signal to noise. In addition, the number of rows can be 2 or more in order to control the physical area covered by the sampling subsystem. The total number of potential illumination fibers can depend on the physical size of emissive area of the light source and the diameter of each fiber. Multiple light sources can be used in the illumination subsystem 100 to increase the number of illumination fibers. The number of collection fibers can depend on the area of the interface to the spectrometer subsystem 300. If the number of collection fibers results in an area larger than the spectrometer subsystem 300 interface allows, a light pipe or other homogenizer followed by an aperture can be used to reduce the size of the output area of the sampling subsystem. The light pipe or other homogenizer can encourage that each collection fiber contributes substantially equally to the light that passes through the aperture.

Figure 13:
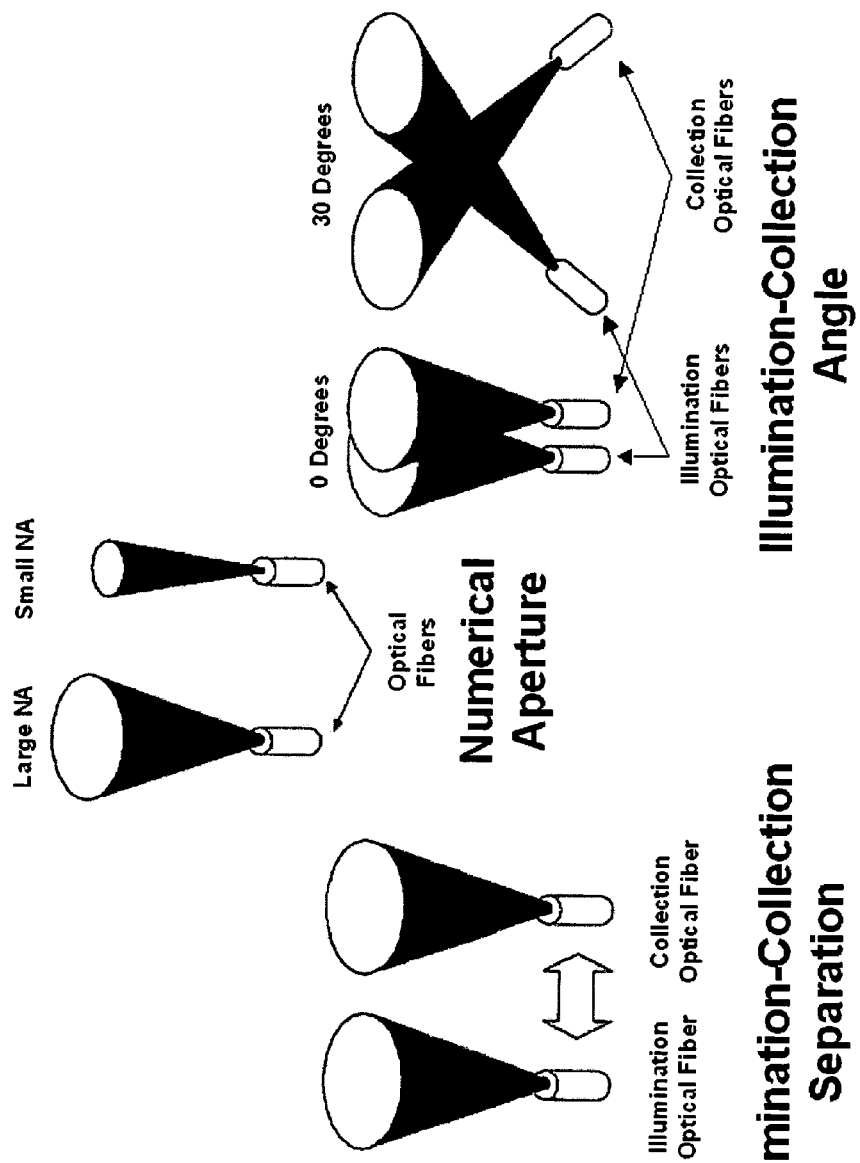
FIG. 13 depicts various aspects of a sampler orientation.
Figure 14:
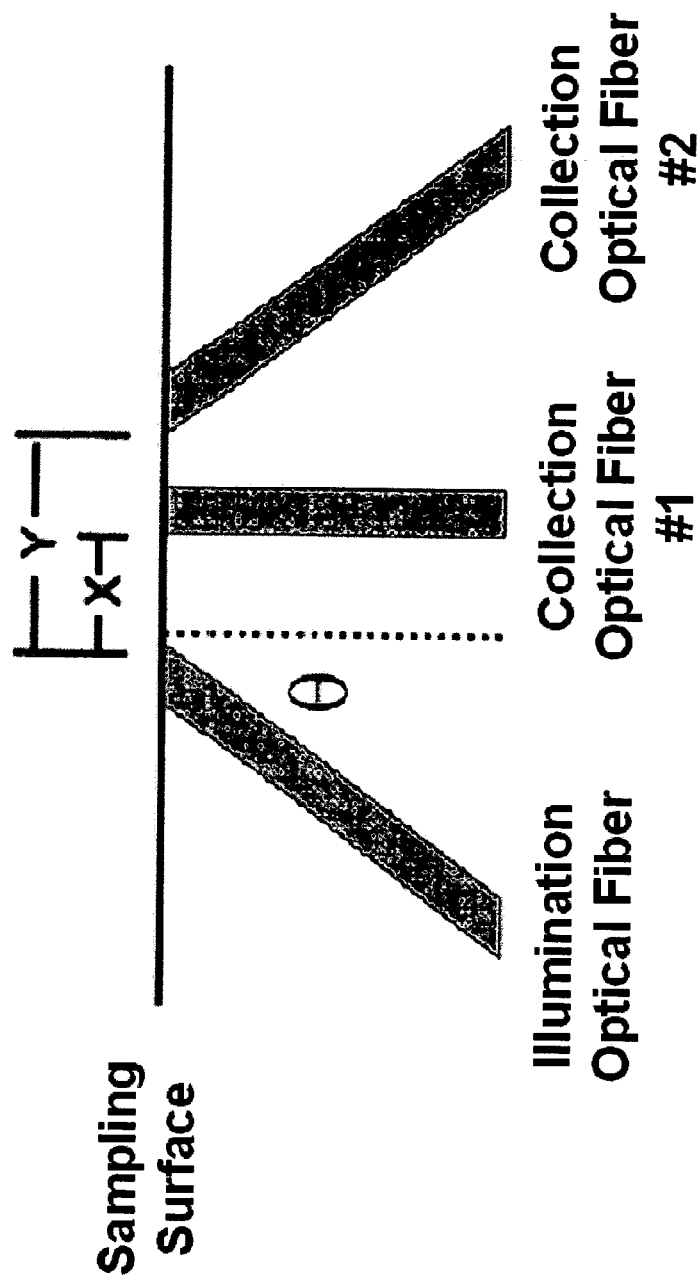
FIG. 14 is a diagramed view of a two-channel sampling subsystem.

The sampling subsystem can use one or more channels, where a channel refers to a specific orientation of the illumination and collection fibers. An orientation is comprised of the angle of the illumination fiber or fibers, the angle of the collection fiber or fibers, the numerical aperture of the illumination fiber or fibers, the numerical aperture of the collection fiber or fibers, and the separation distance between the illumination and collection fiber or fibers. FIG. 13 is a diagram of parameters that form an orientation. Multiple channels can be used in conjunction, either simultaneously or serially, to improve analyte measurements. FIG. 14 is a diagram of a two channel sampling subsystem. Each channel provides a measurement of the sample from a different perspective. The second perspective can help to provide additional spectroscopic information that helps to decouple the signals due to scattering, absorption, and topical interferents on the skin surface. Each of the fibers can have a different numerical aperture and angle (θ). The distances between fibers, X and Y, determine the source-receiver separation. Referring to FIG. 14, the group of fibers (1 source, 1 receiver #1, and 1 receiver #2 in this example) can be replicated 1 to N times in order to increase the sampler area and improve optical efficiency. Furthermore, an additional source channel can be added that creates a 4-channel sampling subsystem. Those skilled in the art will appreciate many variations contemplated by the present invention and illustrated by the examples discussed.

In practice, reflectance measurements obtained from a given channel are comprised of many photons that have traveled a range of pathlengths (all photons do not travel the same distance due to scattering effects). The collective behavior of photon pathlength for a given channel can be characterized by a pathlength distribution, which defines the probability as a function of pathlength. The specific design parameters of a sampling channel can strongly influence the pathlength distribution.

In a single channel sampling subsystem, the spectroscopic effects of concentration and pathlength can be similar. In such cases, the combination of multiple channels into a sampling subsystem can provide the ability to decouple the confounding effects of concentration and photon pathlength through tissue. For example, the concentration of water is presumed constant (albeit unknown) for all channels during the acquisition of the spectroscopic signal. The channels are then selected such that they interrogate essentially the same tissue volume but with different pathlength distributions through the tissue. Thus concentration is held constant while pathlengths are varied which allows the isolation of the spectroscopic effect of pathlength on the measurement. The number of channels can be determined by the cost and performance requirements of the system, and can range from 1 to any number of channels.

As mentioned above, light propagation through tissue is a complex function of the sampling subsystem design, physiological variables, and wavenumber. Consequently, the pathlength of light through tissue has a wavenumber dependence that is not encountered in scatter-free transmission measurements. In order to account for the wavenumber dependence, the interaction of the optical tissue sampler with the scattering properties of human tissue can be modeled via Monte-Carlo simulation using a commercial optical ray-tracing software package (e.g., TracePro). Using the resulting model of the photon-tissue interactions, an estimate of the effective pathlength of light through the dermis and subcutaneous tissue layers as a function of wavenumber can be generated. The effective pathlength ($l_{eff}$) is defined as $$l_{eff}(v) = \frac{\sum_{i=1}^{N} l_i \exp(-\mu_a(v) l_i)}{\sum_{i=1}^{N} l_i} \quad \text{(eq. 1)}$$

where v is wavenumber, $l_i$ is the pathlength traversed by the $i^{th}$ ray in the Monte Carlo simulation [mm], N is the total number of rays in the simulation, and $\mu_a$ is the (wavenumber-dependent) absorption coefficient [mm$^{-1}$]. For the purposes of the effective pathlength calculation in the above example, the absorption coefficients used were those of water at physiological concentrations. One skilled in the art recognizes that $l_i$ can take the form specified by a pathlength distribution (specified above), thus allowing a pathlength distribution to be expressed as an effective pathlength versus wavenumber.

In addition to the use of optical fibers, the sampling subsystem can use a non-fiber based arrangement that places a pattern of input and output areas on the sample surface. In some embodiments, the input and output elements of the sampling subsystem can be comprised of a lens system. In a preferred embodiment, the input element and output element comprise a single lens system that is utilized for both input of light from the energy source and the collection of both specularly and diffusely reflected light from the sample. Alternatively, the input element and output element can comprise two lens systems, placed on opposing sides of an analyte-containing sample, wherein light from the energy source is transmitted to the input element and onto the sample, and light transmitted through the analyte-containing sample then passes through the output element to the spectrum analyzer. Proper masking of the non-fiber based tissue sampling interface ensures that the input light travels a minimum distance in the tissue and contains valid attribute information.

The spectrometer subsystem 300 can be comprised of a variety of different technologies and approaches including interferometers (e.g., Michelson, mock, Sagnac) and dispersive spectrometers (e.g., diffraction gratings, prisms). As demonstrated in FIGS. 6 and 7, any of these spectrometer types can be placed before or after the sampling subsystem. In some embodiments of the orientation shown in FIG. 7 the illumination 1000 and spectrometer 300 subsystems can be combined. In these embodiments, the combined illumination-spectrometer subsystem comprises one or more sources of specific wavelengths of light and some means to combine them. One example embodiment comprises multiple, individually addressed, sources (e.g. laser diodes, Vertical Cavity Emitting Laser (VCSEL), Quantum Dots, and/or Light Emitting Diodes (LEDs)) that illuminate the tissue directly. The tissue then serves as the means to combine the various wavelengths. In other embodiments, the light emitted by the individual sources is combined with a dedicated device such as an integrating chamber, light pipe or homogenizer, or a dispersive element (prism or grating). This device combines the multiple sources into a single output beam. Alternatively, a single, tunable narrow band source (e.g. a vertical cavity surface emitting laser, tunable diode or diode laser) can be used by scanning through its range of tunable wavelengths.

In such embodiments, each source can be modulated in time at a frequency that differs from the other sources in the subsystem. The modulation process can be accomplished with semiconductor light sources that can be rapidly turned on and off at a variety of frequencies. The combined beam, that contains the various wavelengths that have been uniquely modulated, is equivalent in purpose to the beam that would be obtained from a single broadband source that is subsequently modulated or dispersed by a dedicated spectrometer subsystem. The combined beam can be introduced to the tissue sampling subsystem and ultimately the detector in the data acquisition subsystem. The data acquisition subsystem then decodes the signal into its individual wavelength components via an appropriate technique such as a Fourier or Hadamard transform.

New characteristics and advantages of the invention covered by this document have been set forth in the foregoing description. It will be understood, however, that this disclosure is, in many respects, only illustrative. Changes can be made in details, particularly in matters of shape, size, and arrangement of parts or steps, without exceeding the scope of the invention. The scope of the invention is, of course, defined in the language in which the appended claims are expressed.

Methods for Determining Alcohol Concentration from the Spectroscopic Signal

The Beer-Lambert law is commonly invoked in absorption spectroscopy to elucidate the relationship between the measured signal and the property of interest (alcohol concentration). For a sample containing a single absorbing analyte that is spectroscopically measured at a single wavelength, the Beer-Lambert Law can be expressed as:

$$A_\lambda = \epsilon_\lambda l c \quad \text{(eq. 2)}$$

where $A_\lambda$ is the absorption of the sample at wavelength $\lambda$, $\epsilon_\lambda$ is the absorptivity of the single analyte in the sample at wavelength $\lambda$, $l$ is the pathlength that the light travels through the sample, and $c$ is the concentration of the analyte. As such, the Beer-Lambert Law states that a linear relationship between the absorbance of the sample and the concentration of the analyte in the sample. In order to determine the concentration of the analyte in practice, $\epsilon_\lambda$ and $l$ must be known quantities such that upon experimental measurement of $A_\lambda$, the concentration (c) is the only remaining unknown.

The Beer-Lambert Law can be extended to samples containing more than one analyte; however, additional wavelengths must be measured in order to determine the property of interest. For example, a sample containing 2 analytes must be measured at two wavelengths according to the following equations:

$$A_{\lambda 1} = \epsilon_{\alpha \lambda 1} l c_\alpha + \epsilon_{\beta \lambda 1} l c_\beta \text{ and } A_{\lambda 2} = \epsilon_{\alpha \lambda 2} l c_\alpha + \epsilon_{\beta \lambda 2} l c_\beta \quad \text{(eqs. 3 and 4)}$$

where $\alpha$ and $\beta$ represent the 2 analytes and $\lambda 1$ and $\lambda 2$ are the two measured wavelengths. From a mathematical perspective, the number of unknowns (concentrations) in the system of equations can never exceed the number of equations, thus necessitating the measurement of additional wavelengths (to add more equations) and complete characterization of the sample (all $\epsilon$ terms must be separately determined and the pathlength $l$ must be known). This places a significant burden on the direct application of the Beer-Lambert Law and similar direct solution methods such as Classical Least Squares (CLS) as all analytes present in the sample must be identified and their absorptivities determined.

Spectral measurements of complex media, such as human tissue, can be comprised of many overlapping spectral signatures from a large number of chemical analytes. While feasible in some situations depending on the measurement objectives, the Beer-Lambert/CLS class of approaches can be difficult to implement due to the large number of variables. In such cases, alternative multivariate analysis methods can be used to decouple the signal of the analyte of interest from the signals of other analytes in the system (interferents). Partial Least Squares (PLS) regression is a well established multivariate analysis method that has been applied to quantitative analysis of spectroscopic measurements and will be used for demonstrative purposes for the remainder of the disclosure. However, other multivariate analysis methods such as Principal Components Regression (PCR), Ridge Regression, Multiple Linear Regression (MLR) and Neural Networks are also suitable for the present invention. One skilled in the art will recognize that other methods of similar functionality can also be applicable.

In PLS regression, a set of spectroscopic calibration measurements is acquired where each spectroscopic measurement has a corresponding reference value for the property of interest (e.g. blood alcohol concentration). The calibration spectral data are then decomposed into a series of factors (spectral shapes that are sometimes called loading vectors or latent variables) and scores (the magnitude of the projection of each spectrum onto a given factor) such that the squared covariance between the reference values and the scores on each successive PLS loading vector is maximized. The scores of the calibration spectra are then regressed onto the reference values in a multiple linear regression (MLR) step in order to calculate a set of spectral weights (one weight per wavenumber in the spectra) that minimizes the analyte measurement error of the calibration measurements in a least-squares sense. These spectral weights are called the regression vector of the calibration model. Once the calibration model is established, subsequent measurements are obtained by calculating the vector dot product of the regression vector and each measured spectrum.

An advantage of PLS and similar methods (commonly referred to as indirect methods) is that the $\epsilon$ terms in the Beer-Lambert Law (and thus the complete composition of the sample) do not need to be known. Furthermore, inverse methods tend to be more robust at dealing with nonlinearities in the spectral measurement such as those caused by instrumental drift, light scattering, environmental noise, and chemical interactions.

Figure 15:
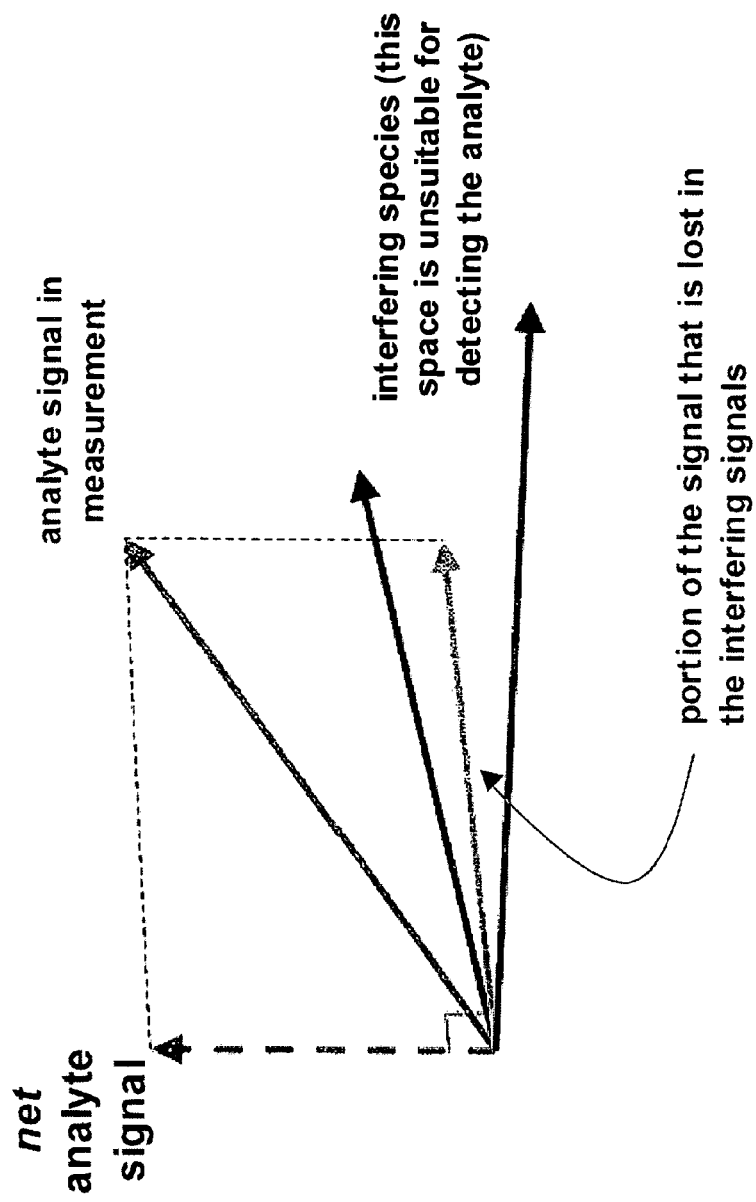
FIG. 15 is a diagram of the net analyte signal (NAS) for a 3 component system.

Functionally, the goal of the multivariate calibration (PLS or otherwise) in the present invention is to determine the part of the spectroscopic signal of alcohol that is effectively orthogonal (contravariant) to the spectra of all interferents in the sample. This part of the signal is referred to as the net attribute signal and can be calculated using the regression vector (b) described above using equation 4. If there are no interfering species, the net attribute spectrum is equal to the pure spectrum of alcohol. If interfering species with similar spectra to the attribute are present, the net attribute signal will be reduced relative to the entire spectrum. The concept of net attribute signal for a three-analyte system is depicted graphically in FIG. 15.

$$NAS = \frac{\hat{b}}{\|\hat{b}\|_2^2} \qquad \text{(eq. 5)}$$

In other embodiments of the present invention, a hybrid calibration model can be used to measure the alcohol concentrations of subject spectra. The term hybrid model denotes that a partial least squares (PLS) calibration model was developed using a combination of in vitro and in vivo spectral data. The in vitro portion of the data can comprise a 0.1 mm pathlength transmission spectrum of 500 mg/dL alcohol in water measured using a non-invasive measurement system configured for transmission measurements. The transmission spectrum can be ratioed to a 0.1 mm pathlength transmission spectrum of water, converted to absorbance, and normalized to unit pathlength and concentration.

Figure 16:
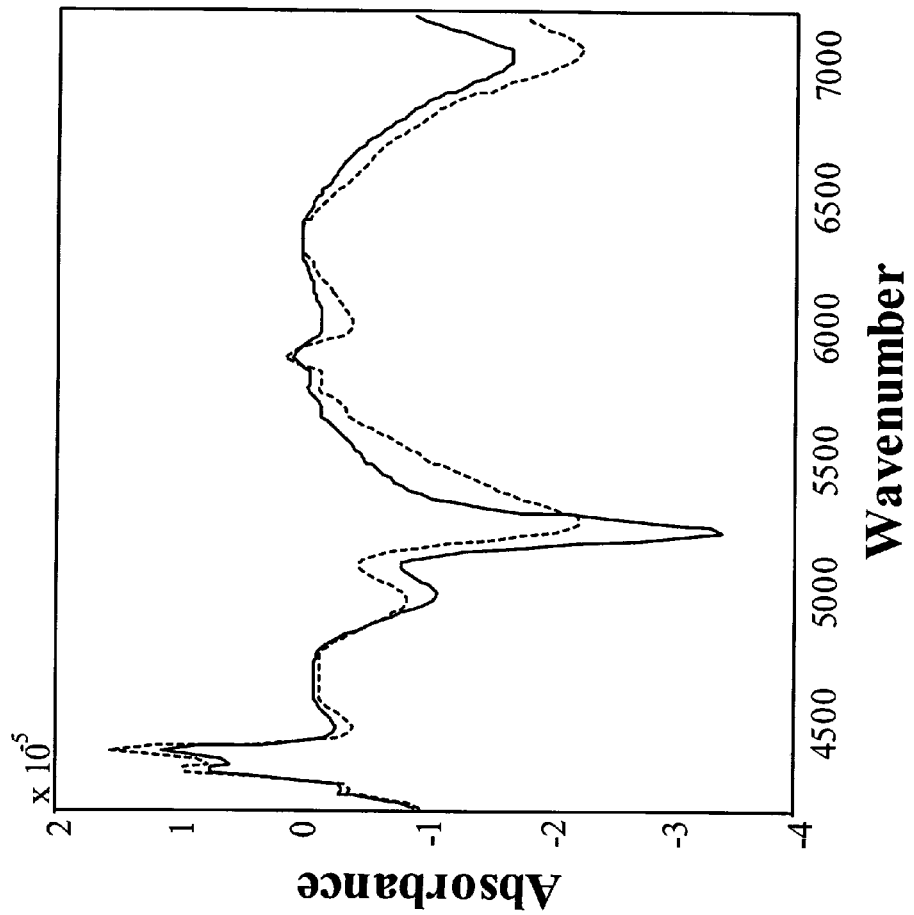
FIG. 16 is a diagram of the near infrared absorptivity of alcohol before and after tissue pathlength correction.

The alcohol absorbance spectrum (as measured in transmission) was then scaled by a computed effective path function (see equation 1) to form a corrected alcohol spectrum representative of the wavenumber dependent pathlength measured by the diffuse reflectance optical sampler. FIG. 16 shows the alcohol absorbance spectrum before and after correction by the path function. This corrected spectrum formed the base spectrum for the mathematical addition of alcohol to the calibration spectra.

Figure 17:
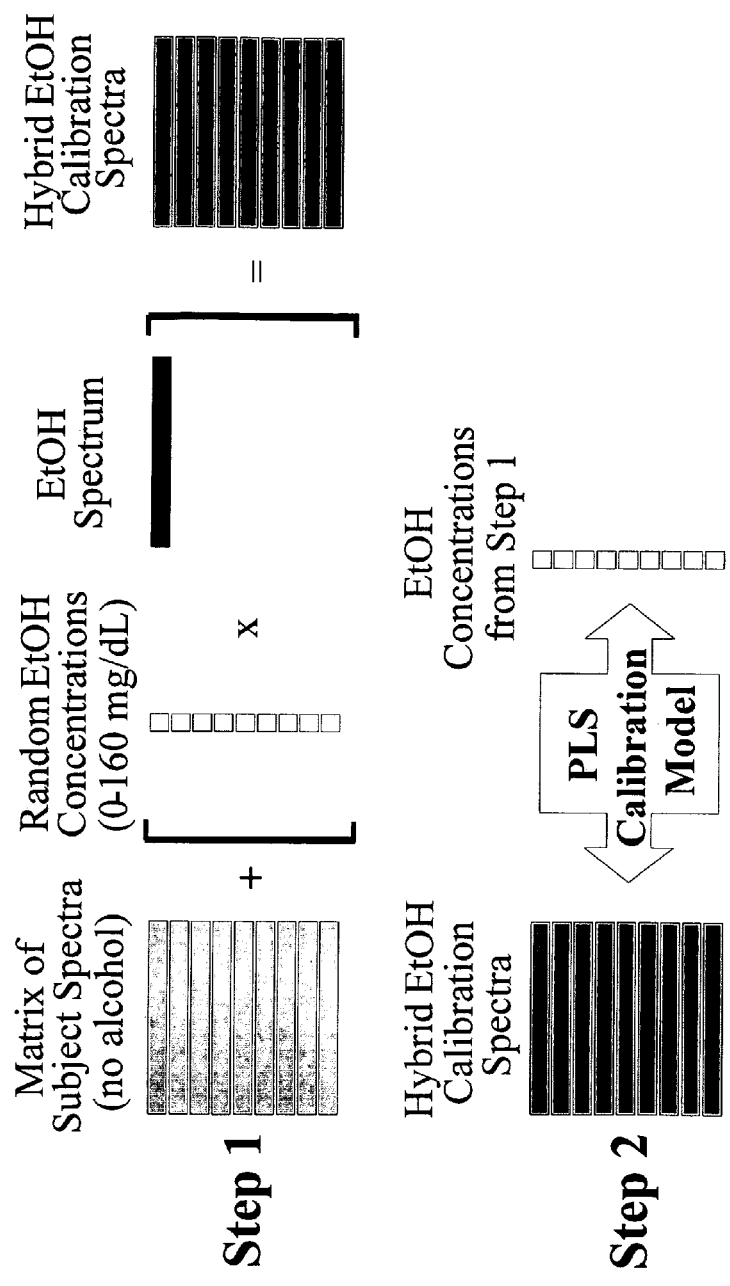
FIG. 17 is a schematic representation of the hybrid calibration formation process.

The in vivo data comprised noninvasive tissue spectra collected from persons who had not consumed alcohol. A hybrid model was formed by adding the alcohol pure component spectrum, weighted by various alcohol "concentrations" (ranging from 0 to 160 mg/dL), to the noninvasive tissue spectral data. The PLS calibration model was built by regressing the synthetic alcohol concentrations on the hybrid spectral data. FIG. 17 is a schematic representation of the hybrid calibration formation process. The hybrid calibration in this work used approximately 1500 non-invasive tissue spectra that were collected from 133 subjects over three months.

The use of hybrid calibration models, rather than calibration models built from spectra acquired from subjects who have consumed alcohol, can provide advantages. The hybrid modeling process makes it possible to generate calibration spectra that contain higher concentrations (up to 160 mg/dL in one example) of alcohol than would be considered safe for consumption in a human subject study (120 mg/dL is generally considered a safe upper limit). The result can be a stronger calibration with a wider range of analyte concentrations that is able to more accurately measure higher alcohol concentrations. This can be important because alcohol concentrations observed in the field can be more than double the maximum safe dosage in a clinical research setting. The hybrid calibration process also allows the prevention of correlations between alcohol and the spectral interferents naturally or artificially present in or on the surface of the tissue, thus generating a regression vector with a larger net attribute signal. For example, the random addition of alcohol signal to the calibration spectra prevents alcohol concentration from being correlated with water concentration. Thus, the hybrid approach reduces the possibility that the measurement could spuriously track changes in tissue water content instead of alcohol concentration.

Alternative calibration strategies can be used in place of, or in conjunction with, the above described methods. For example, in some embodiments biometric enrollment information is acquired from each person to be measured on the device in the future. In such cases, the enrollment measurements can also be used to improve the accuracy and precision of the alcohol or substance of abuse measurement. In this scenario, the calibration spectra are mean-centered by subject (all spectra from a subject are located, the mean of those spectra is subtracted from each, and the "mean centered" spectra are returned to the spectral set). In this manner, the majority of inter-subject spectral differences caused by variations in physiology are removed from the calibration measurements and the range of spectral interferents correspondingly reduced. The centered spectra and associated analyte reference values (blood alcohol concentrations) are then presented to a multivariate analysis method such as partial least squares regression. This process is sometimes referred to as generating an "enrolled", "generic", or "tailored" calibration. Additional details on this approach are described in U.S. Pat. No. 6,157,041, entitled "Methods and Apparatus for Tailoring Spectroscopic Calibration Models," the disclosure of which is incorporated by reference.

In practice, once a future, post calibration, subject is enrolled on a noninvasive device their enrollment spectrum can be subtracted from subsequent measurements prior to determining the alcohol or substance of abuse concentration using the generic calibration model. Similar to the mean-centering by subject operation of the calibration spectra, the subtraction of the enrollment spectrum removes the average spectroscopic signature of the subject while preserving the signal of the analyte of interest (alcohol or substance of abuse). In some embodiments, significant performance advantages can be realized relative to the use of a non-generic calibration method.

Once formed, a calibration (generic or otherwise) should remain stable and produce accurate attribute predictions over a desired period of time. This process is referred to as calibration maintenance and can comprise multiple methods that can be used individually or in conjunction. The first method is to create the calibration in a manner that inherently makes it robust. Several different types of instrumental and environmental variation can affect the measurement capability of a calibration model. It is possible and desirable to reduce the magnitude of the effect of instrumental and environmental variation by incorporating this variation into the calibration model.

It can be difficult, however, to span the entire possible range of instrument states during the calibration period. System perturbations can result in the instrument being operated outside the space of the calibration model. Examples of potentially problematic instrument and environmental variation include, but are not limited to changes in the levels of environmental interferents such as water vapor or $CO_2$ gas, changes in the alignment of the instrument's optical components, fluctuations in the output power of the instrument's illumination system, and changes in the spatial and angular distribution of the light output by the instrument's illumination system. Measurements made while the instrument is in an inadequately modeled state can exhibit measurement errors. In the case of in vivo optical measurements of analyte properties, these types of errors can result in erroneous measurements that degrade the utility of the system. Therefore it is often advantageous to use additional calibration maintenance techniques during the life of the instrument in order to continually verify and correct for the instrument's status.

Calibration maintenance techniques are discussed in U.S. patent application Ser. No. 09/832,608, 'Optically Similar Reference Samples and Related Methods for Multivariate Calibration Models Used in "Optical Spectroscopy," and U.S. patent application Ser. No. 10/281,576, "Optically Similar Reference Samples," and U.S. patent application Ser. No. 10/733,195, "Adaptive Compensation for Measurement Distortions in Spectroscopy," each of which is incorporated herein by reference. These methods use an environmentally inert non-tissue sample, such as an integrating sphere, that optionally contains the attribute of interest, to monitor the instrument over time. The sample can be incorporated into the optical path of the instrument or interface with the sampling subsystem in a manner similar to that of tissue measurements. The sample can be used in transmission or in reflectance and can contain stable spectral features or contribute no spectral features of its own. The material can be a solid, liquid, or gel material as long as its spectrum is stable or predicable over time. Any unexplained change in the spectra acquired from the sample over time indicate that the instrument has undergone a perturbation or drift due to environmental effects. The spectral change can then be used to correct subsequent tissue measurements in humans in order to ensure accurate attribute measurement.

Once a calibration is formed, it is desirable to transfer the calibration to existing and future instruments. This process is commonly referred to as calibration transfer. While not required, calibration transfer prevents the need for a calibration to be built on each system that is manufactured. This represents a significant time and cost savings that could result in the difference between success or failure of a commercial product. Calibration transfer arises from the fact that optical and electronic components can vary from unit to unit which, in aggregate, results in differences in the spectra obtained from multiple instruments. For example, two light sources can have different color temperatures thereby resulting in a different light distribution for the two sources. The responsivity of two detectors can also differ significantly, which can result in additional spectral differences.

Similar to calibration maintenance, multiple methods can be used in order to effectively achieve calibration transfer. The first method is to build the calibration with multiple instruments. The presence of multiple instruments allows the spectral variation associated with instrument differences to be determined and made effectively orthogonal to the attribute signal during the calibration formation process. While this does approach can reduce the net attribute signal, it can be an effective means of calibration transfer.

Additional calibration transfer methods involve explicitly determining the difference in the spectral signature of a system relative to those used to build the calibration. In this case, the spectral difference can then be used to correct a spectral measurement prior to attribute prediction on a system or it can be used to correct the predicted attribute value directly. The spectral signature specific to an instrument can be determined from the relative difference in spectra of a stable sample acquired from the system of interest and those used to build the calibration. Many suitable approaches and algorithms for effective calibration transfer are known in the art; some of which are summarized in "Standardisation and Calibration Transfer for Near Infrared Instruments: a Review", by Tom Fearn in the Journal of Near Infrared Spectroscopy, vol. 8, pp. 229-244 (2001). Note that these approaches and algorithms can be equally suited to other spectroscopic techniques such as Raman measurements. The samples described in the calibration maintenance section can also be applicable to calibration transfer. See, e.g. U.S. Pat. No. 6,441,388, incorporated herein by reference.

Methods for Determining Biometric Verification/Identification from Spectroscopic Signal Biometric identification describes the process of using one or more physical or behavioral features to identify a person or other biological entity. There are two common biometric modes: identification and verification. Biometric identification attempts to answer the question of, "do I know you?" The biometric measurement device collects a set of biometric data from a target individual. From this information alone it assesses whether the person was previously enrolled in the biometric system. Systems that perform the biometric identification task, such as the FBI's Automatic Fingerprint Identification System (AFIS), are generally very expensive (several million dollars or more) and require many minutes to detect a match between an unknown sample and a large database containing hundreds of thousands or millions of entries. In biometric verification the relevant question is, "are you who you say you are?" This mode is used in cases where an individual makes a claim of identity using a code, magnetic card, or other means, and the device uses the biometric data to confirm the identity of the person by comparing the target biometric data with the enrolled data that corresponds with the purported identity. The present apparatus and methods for monitoring the presence or concentration of alcohol or substances of abuse in controlled environments can use either biometric mode.

There also exists at least one variant between these two modes that is also suitable for use in the present invention. This variant occurs in the case where a small number of individuals are contained in the enrolled database and the biometric application requires the determination of only whether a target individual is among the enrolled set. In this case, the exact identity of the individual is not required and thus the task is somewhat different (and often easier) than the identification task described above. This variant might be useful in applications where the biometric system is used in methods where the tested individual must be both part of the authorized group and sober but their specific identity is not required. The term "identity characteristic" includes all of the above modes, variants, and combinations or variations thereof.

There are three major data elements associated with a biometric measurement: calibration, enrollment, and target spectral data. The calibration data are used to establish spectral features that are important for biometric determinations. This set of data consists of series of spectroscopic tissue measurements that are collected from an individual or individuals of known identity. Preferably, these data are collected over a period of time and a set of conditions such that multiple spectra are collected on each individual while they span nearly the full range of physiological states that a person is expected to go through. In addition, the instrument or instruments used for spectral collection generally should also span the full range of instrumental and environmental effects that it or sister instruments are likely to see in actual use. These calibration data are then analyzed in such a way as to establish spectral wavelengths or "factors" (i.e. linear combinations of wavelengths or spectral shapes) that are sensitive to between-person spectral differences while minimizing sensitivity to within-person, instrumental (both within- and between-instruments), and environmental effects. These wavelengths or factors are then used subsequently to perform the biometric determination tasks.

The second major set of spectral data used for biometric determinations is the enrollment spectral data. The purpose of the enrollment spectra for a given subject or individual is to generate a "representation" of that subject's unique spectroscopic characteristics. Enrollment spectra are collected from individuals who are authorized or otherwise required to be recognized by the biometric system. Each enrollment spectrum can be collected over a period of seconds or minutes. Two or more enrollment measurements can be collected from the individual to ensure similarity between the measurements and rule out one or more measurements if artifacts are detected. If one or more measurements are discarded, additional enrollment spectra can be collected. The enrollment measurements for a given subject can be averaged together, otherwise combined, or stored separately. In any case, the data are stored in an enrollment database. In some cases, each set of enrollment data are linked with an identifier (e.g. a password or key code) for the persons on whom the spectra were measured. In the case of an identification task, the identifier can be used for record keeping purposes of who accessed the biometric system at which times. For a verification task, the identifier is used to extract the proper set of enrollment data against which verification is performed.

The third and final major set of data used for the biometric system is the spectral data collected when a person attempts to use the biometric system for identification or verification. These data are referred to as target spectra. They are compared to the measurements stored in the enrollment database (or subset of the database in the case of identity verification) using the classification wavelengths or factors obtained from the calibration set. In the case of biometric identification, the system compares the target spectrum to all of the enrollment spectra and reports a match if one or more of the enrolled individual's data is sufficiently similar to the target spectrum. If more than one enrolled individual matches the target, then either all of the matching individuals can be reported, or the best match can be reported as the identified person. In the case of biometric verification, the target spectrum is accompanied by an asserted identity that is collected using a magnetic card, a typed user name or identifier, a transponder, a signal from another biometric system, or other means. The asserted identity is then used to retrieve the corresponding set of spectral data from the enrollment database, against which the biometric similarity determination is made and the identity verified or denied. If the similarity is inadequate, then the biometric determination is cancelled and a new target measurement may be attempted.

In one method of verification, principle component analysis is applied to the calibration data to generate spectral factors. These factors are then applied to the spectral difference taken between a target spectrum and an enrollment spectrum to generate Mahalanobis distance and spectral residual magnitude values as similarity metrics. Identify is verified only if the aforementioned distance and magnitude are less than a predetermined threshold set for each. Similarly, in a preferred method for biometric identification, the Mahalanobis distance and spectral residual magnitude are calculated for the target spectrum relative each of the database spectra. The identify of the person providing the test spectrum is established as the person or persons associated with the database measurement that gave the smallest Mahalanobis distance and spectral residual magnitude that is less than a predetermined threshold set for each.

In a preferred method, the identification or verification task is implemented when a person seeks to perform an operation for which there are a limited number of people authorized (e.g., perform a spectroscopic measurement, achieve enter a controlled facility, pass through an immigration checkpoint, etc.). The person's spectral data is used for identification or verification of the person's identity. In this preferred method, the person initially enrolls in the system by collecting one or more representative tissue spectra. If two or more spectra are collected during the enrollment, then these spectra can be checked for consistency and recorded only if they are sufficiently similar, limiting the possibility of a sample artifact corrupting the enrollment data. For a verification implementation, an identifier such as a PIN code, magnetic card number, username, badge, voice pattern, other biometric, or some other identifier can also be collected and associated with the confirmed enrollment spectrum or spectra.

In subsequent use, biometric identification can take place by collecting a spectrum from a person attempting to gain authorization. This spectrum can then be compared to the spectra in the enrolled authorization database and an identification made if the match to an authorized database entry was better than a predetermined threshold. The verification task is similar, but can require that the person present the identifier in addition to a collected spectrum. The identifier can then be used to select a particular enrollment database spectrum and authorization would be granted if the current spectrum is sufficiently similar to the selected enrollment spectrum. If the biometric task is associated with an operation for which only a single person is authorized, then the verification task and identification task are the same and both simplify to an assurance that the sole authorized individual is attempting the operation without the need for a separate identifier.

The biometric measurement, regardless of mode, can be performed in a variety of ways including linear discriminant analysis, quadratic discriminant analysis, K-nearest neighbors, neural networks, and other multivariate analysis techniques or classification techniques. Some of these methods rely upon establishing the underlying spectral shapes (factors, loading vectors, eigenvectors, latent variables, etc.) in the intra-person calibration database, and then using standard outlier methodologies (spectral F ratios, Mahalanobis distances, Euclidean distances, etc.) to determine the consistency of an incoming measurement with the enrollment database. The underlying spectral shapes can be generated by multiple means as disclosed herein.

First, the underlying spectral shapes can be generated based upon simple spectral decompositions (eigen analysis, Fourier analysis, etc.) of the calibration data. The second method of generating underlying spectral shapes relates to the development of a generic model as described in U.S. Pat. No. 6,157,041, entitled "Methods and Apparatus for Tailoring Spectroscopic Calibration Models," the disclosure of which is incorporated by reference. In this application, the underlying spectral shapes are generated through a calibration procedure performed on intra-person spectral features. The underlying spectral shapes can be generated by the development of a calibration based upon simulated constituent variation. The simulated constituent variation can model the variation introduced by real physiological or environmental or instrumental variation or can be simply be an artificial spectroscopic variation. It is recognized that other means of determining underlying shapes would be applicable to the identification and verification methods of the present invention. These methods can be used either in conjunction with, or in lieu of the aforementioned techniques.

Methods for Performing Actions in Controlled Environments

The signal required to perform the action can be wireless or wired as deemed appropriate for the application. Furthermore, in some embodiments, wireless communication can also be used to report the measurement results or the operational status of the monitoring device to a central monitoring, security, maintenance, or law enforcement facility. One skilled in the art will appreciate the wide variety of environments and systems that could feasibly incorporate or function as the analyte monitoring device of the present invention.

Figure 18:
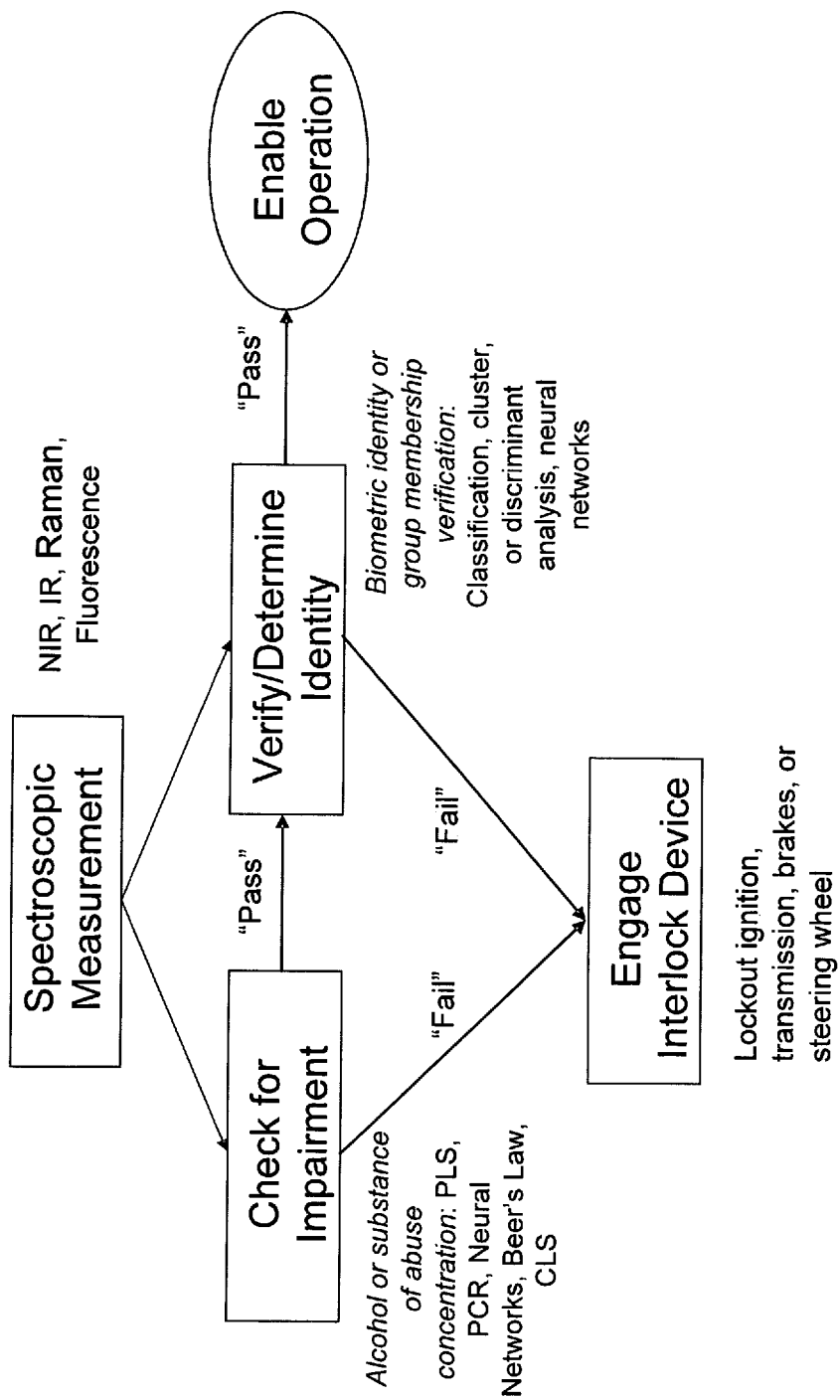
FIG. 18 is a diagram of an example embodiment according to the present invention.
Figure 19:
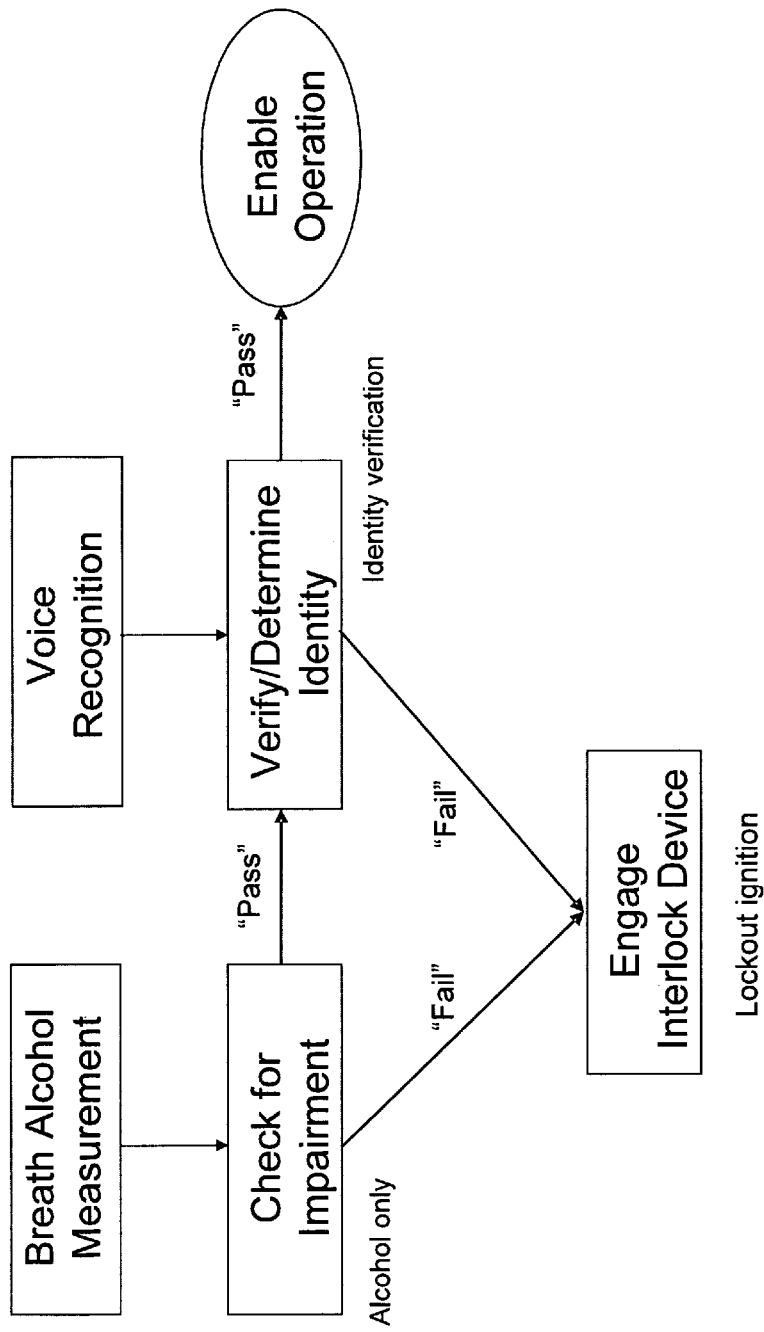
FIG. 19 is a diagram of an example embodiment according to the present invention.

FIG. 18 shows an embodiment of the present invention where a single spectroscopic measurement is used to determine the presence or concentration of an analyte and verify identity of the tested individual. A significant advantage of the present invention is the potential to detect impairment caused by alcohol and/or substances of abuse rather than alcohol alone which significantly increases the utility of the present invention. FIG. 19 shows another example embodiment, with spectroscopic analyte measurement used in combination with voice recognition (or other) identity determination or verification.

Remote Storage of Enrollment Data/SmartKeys

Additional security, convenience, and policy control may be achieved by storing an individual's biometric data on an external communication device rather than internally in a given measurement device. A "smartkey" which can comprise an electronic storage and communication device can store, encrypt, and securely communicate data to the measurement device: For example, in some embodiments the smartkey can enable physical access control to a facility by utilizing a digital two key authentication scheme. The first key can be an authorized electronic access code which is specific to a facility that the user is authorized to enter. The second key can be linked to the individual's enrollment data which requires that only the authorized individual use that key. This type of system has several advantages:

First, the system can use existing technology which has been developed for secure encryption, data transmission, and authentication transactions using smart cards/tokens. Second, in applications where an individual might be required to frequently move between multiple secure locations the use of a smartkey to store biometric data allows centralized administration of both location specific and user specific security and alcohol/substance of abuse policies. An individual can be enrolled in an administrator's office or specified location on a master device and the resulting enrollment information and individual specific security policy can be encoded on that individual's key. The individual can then perform alcohol and biometric measurements on multiple devices, even if the individual has never before used that specific device. An additional advantage of some embodiments is that centralized administration tasks, e.g. restricting or revoking an individual's privileges, can be handled using a single database. Security policy updates can be relayed to the appropriate devices in other locations via RF uplinks or other electronic transmission means. In some embodiments, the use of RF communication and an individual's smartkey can provide rapid, seamless access to a facility via the touch based biometric verification step. No access codes are required from the individual.

Third, in applications where updated enrollment is desired, such as restricted access to multiple buildings in a large facility, an individual's enrollment data may become out of date at a given location that he or she seldom uses. By storing the enrollment data on a user specific smartkey, the individual can always maintain the most current enrollment information regardless of the testing location. In some embodiments, profile updates can be handled via two-way communication with the smartkey upon successful biometric identity verification. Finally, concerns regarding the theft, manipulation, or dissemination of an individual's biometric identity information is greatly reduced as only a single copy of that data exists, in a secure, encrypted format, under physical control of the individual at all times.

Some embodiments for remotely storing enrollment data are comprised of a means for storing data, a means for providing power, a means for communication and data transfer. The means for storing data can be any electronic or magnetic storage media consistent with the form factor desired. Some example embodiments of the means for providing power include, but are not limited to, a battery or external RF power via the communication uplink. Some example embodiments of the means for communication and data transfer include, but are not limited to, serial or other secure data protocol via RF, optical, sonic, or direct electrical connections. These components can be combined in many possible form factors. Some examples include car key, plastic transponder, credit card style smart card, employee id badge, lapel pin, etc.

One application that could benefit from the transfer of enrollment data is networks of remote, unattended monitoring systems. In one embodiment, the network could be comprised of one or more kiosks located in multiple locations. In this type of scenario, an individual that is required to check-in and provide proof of conformance to alcohol or substance of abuse restrictions could find the nearest kiosk that is part of the network. In this case, the individual's enrollment data could be provide by the SmartKey embodiment above or transferred to the kiosk via another kiosk or central station using any of a variety of means such as wireless, telephone line, cable line, fiber optics, or any other means of data transfer. In this scenario, the remote kiosk would verify that the purported individual is being tested and subsequently screen or test for alcohol and/or substances of abuse. Such approaches could provide improved flexibility and increased testing frequency relative to tests performed at a single facility.

Experimental Results: Alcohol

Two clinical studies were performed in order to demonstrate the alcohol measurement capability of the present invention. The first was a calibration study based upon the hybrid calibration model approach described above. The in vitro portion of the data was a 1.0 mm pathlength spectrum of 501.65 mg/dL alcohol in water measured in transmission. The spectrum was ratioed to a 1.0 mm pathlength transmission spectrum of carbon tetrachloride and converted to absorbance. The contribution of water to the 501.65 mg/dL alcohol spectrum was removed by subtracting an absorbance spectrum of pure water scaled to the appropriate concentration to account for the displacement effects of alcohol. Given the level of dilution of the alcohol solution, this is a reasonable first approximation since water is the dominant component of the matrix and is likely not significantly affected (in a chemical sense) by the presence of the minute quantity of alcohol. The resulting water-corrected 501.65 mg/dL alcohol spectrum was normalized to unit pathlength and concentration (absorptivity per mg/dL) and pathlength scaled for tissue as shown in FIG. 16.

The in vivo calibration data consisted of noninvasive tissue spectra collected from individuals who had not consumed alcohol. The hybrid model spectra were formed by adding the alcohol pure component spectrum at various simulated alcohol "concentrations" according to the schematic process shown in FIG. 17. The concentration for each simulated spectrum was simply drawn randomly from a uniform distribution spanning the expected range of alcohol concentrations in vivo (0 to 160 mg/dL). Each spectrum was treated as completely independent of all others, so no inter- or intra-subject differences or time dependencies were incorporated in the concentration assignments. A partial least squares (PLS) calibration model was built by regressing the synthetic alcohol concentrations on the hybrid calibration spectral data. The hybrid calibration contained approximately 1500 noninvasive NIR measurements collected from 133 subjects over three months.

The second study was a prospective validation experiment where ten volunteer subjects were measured in a clinical laboratory over a period of 5 days to assess the noninvasive alcohol measurement accuracy relative to blood and breath alcohol measurements. None of these ten subjects participated in the calibration experiment, so they represented an objective and prospective assessment of the noninvasive NIR measurement performance. Subjects were consented according to an IRB-approved protocol. Alcohol doses were administered to achieve peak blood alcohol concentration (BAC) values of 120 mg/dL (0.12%) assuming ingested alcohol would be completely absorbed into the bloodstream. The subjects were asked to consume the total alcohol dose within a 20-minute time period.

Baseline capillary blood, breath, and noninvasive alcohol measurements were acquired from each subject upon arrival in order to verify zero initial blood alcohol concentration. The blood measurements were acquired using a Yellow Springs Incorporated 2700 Select blood analyzer (YSI). Breath testing was accomplished using an Intoximeters EC/IR in "quick test" mode. Each subject then consumed his or her alcohol dose. Repeated cycles of blood, breath, and noninvasive measurements were then acquired to monitor alcohol concentration throughout each subject's alcohol excursion (about 10-12 minutes per cycle). A total of 372 sets of noninvasive, blood, and breath alcohol measurements were acquired from the 10 subjects in the validation study.

Figure 20:
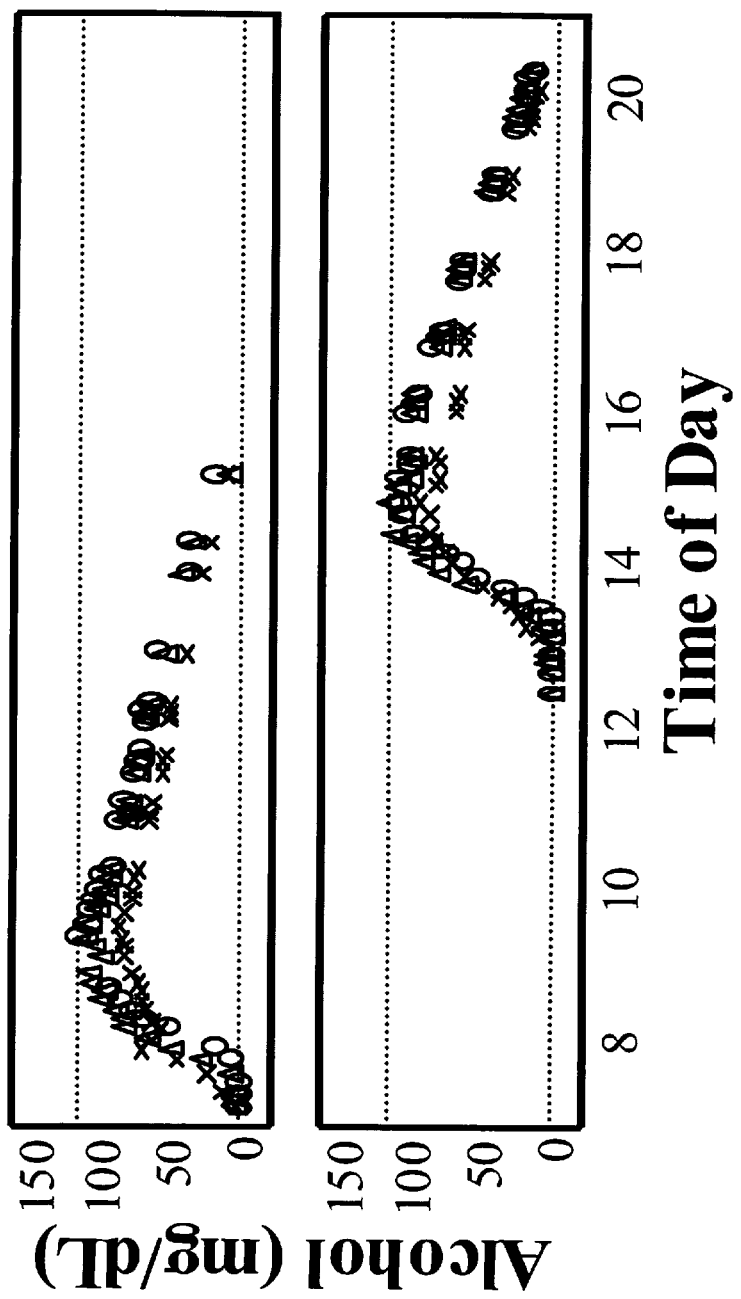
FIG. 20 shows blood, breath, and non-invasive alcohol (obtained from the present invention) over time for two subjects during induced alcohol excursions.
Figure 21:
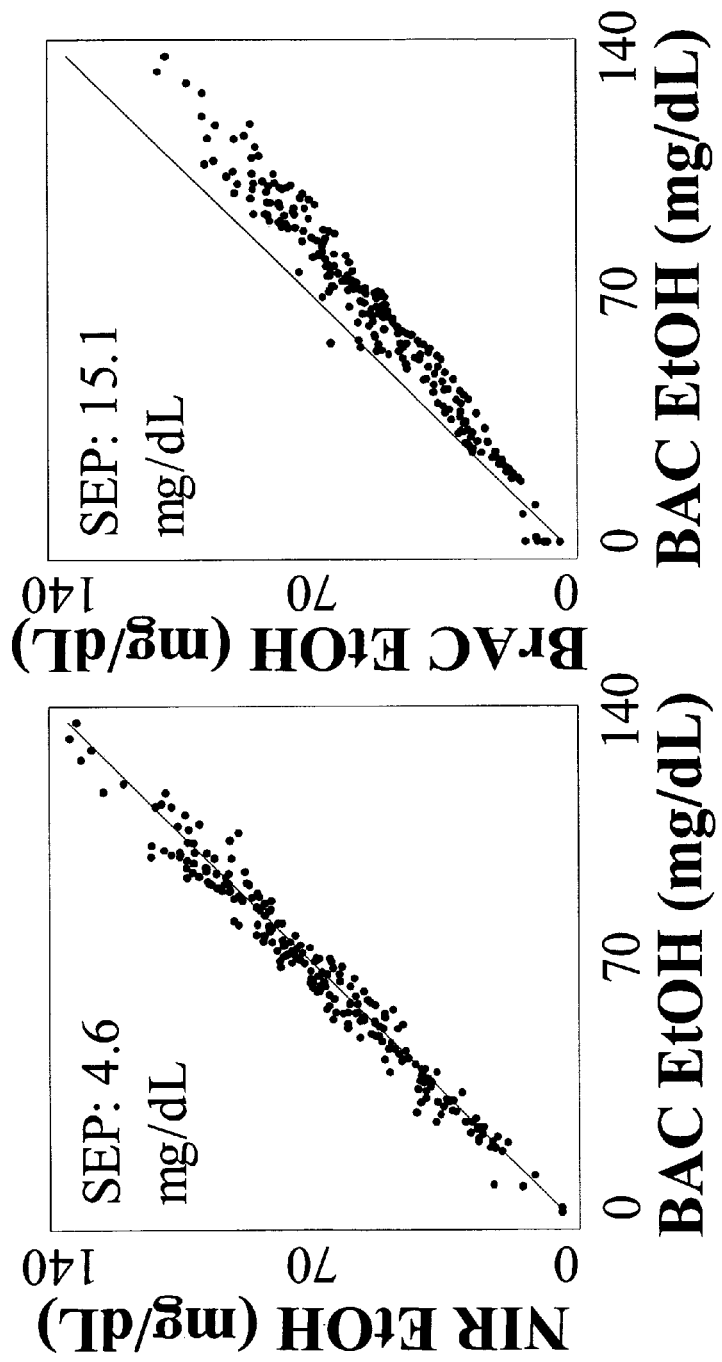
FIG. 21 is a graph of non-invasive alcohol measurements versus blood alcohol reference for multiple human subjects that demonstrates the ability of the system of the present invention to derive clinically relevant alcohol measurements.

FIG. 20 depicts the alcohol measurements acquired from two of the 10 validation subjects during their induced alcohol excursions. Each window contains the blood, breath, and noninvasive alcohol concentrations versus time that were measured during the alcohol excursion for that subject. FIG. 21 shows a side-by-side comparison of the noninvasive spectroscopic alcohol measurements of the present invention versus blood (BAC) alcohol and breath (BrAC) versus blood (BAC) alcohol that were acquired from the 10 study subjects. Examination of FIG. 19 demonstrates that the breath measurements exhibit a proportional error relative to blood alcohol. This is due to the globally applied blood-breath partition coefficient of 2100 mg EtOH/dL blood per mg EtOH/dL air that relates the concentration of alcohol in expired air from the lungs to blood alcohol. The comparison of the breath and non-invasive measurements demonstrates that under identical experimental conditions the precision of the current invention's measurement is substantially equal to that of a commonly used state-of-the-art breath alcohol instrument. In addition, the non-invasive measurement accuracy is superior to the breath measurement because it does not exhibit a proportional error.

Experimental Results: Biometric

An experiment was conducted to determine the viability of utilizing the methodology disclosed herein to verify the identification of an individual using near infrared spectroscopic measurements of skin tissue. The design of the instrumentation used was identical to that described for the experimental alcohol results discussed above. The sampling of the human tissue was done on the volar side of the forearm, consistent with the alcohol experiment. Spectra were acquired, and the recorded 4,200 to 7,200 cm$^{-1}$ NIR spectra converted to absorbance. The spectra consisted of two distinct sets. The first set was a calibration set comprised of 10,951 noninvasive spectroscopic measurements acquired from 209 subjects. On average, approximately 5 measurements were acquired from each subject for each of approximately 10 days. The second set of spectra was a validation set comprised of 3,159 noninvasive spectral measurements from 37 subjects. Each subject was measured approximately 85 times over a 2 month period.

The calibration spectra were processed to produce generic data as described in U.S. Pat. No. 6,157,041, entitled "Methods and Apparatus for Tailoring Spectroscopic Calibration Models," incorporated herein by reference. A PCA decomposition of these data was performed to generate 50 factors (also called latent variables, loadings, or eigenvectors) and associated scores (also called weights or eigenvalues). The validation measurements were then split into enrollment and test sets. The enrollment set was comprised of 37 spectra that were obtained by averaging the first three measurements acquired from each of the 37 validation subjects. The test set was comprised of the remaining validation spectra.

In order to evaluate the ability of the present invention to correctly verify the identity of a person, the enrollment spectrum of each subject was subtracted from his or her spectra in the test set. The Mahalanobis distances of the resulting "authorized" spectral differences were then calculated using the calibration factors and scores. In order to evaluate the ability to correctly reject "intruders" (an unauthorized person who claims to be authorized in order enter or leave a controlled environment), the enrollment spectrum for a given subject was subtracted from the test spectra for the other 36 validation subjects. This was done for each validation subject in round-robin fashion in order to test all possible enrollment/test permutations. Similar to the "authorized" case, the Mahalanobis distance for each of the resulting "intruder" difference spectra was computed relative to the calibration factors and scores.

The "authorized" and "intruder" Mahalanobis distances were then used to examine the biometric performance of the spectroscopic method using multiple distance thresholds. In this framework, if the distance of a given spectral difference (whether from the "authorized" or "intruder" group) is less than the threshold distance, then the purported identity is verified. The case where an "authorized" spectral difference is below the threshold (and the identity verified) is referred to as a "True Accept" (also called a True Positive or True Admission). The case where an "authorized" spectral difference is above the threshold (the device erroneously rejects an authorized user) is referred to as a "False Reject" or "False Negative". Similarly, a "True Reject" or "True Negative" occurs when an "intruder" distance is above the threshold and a "False Accept" occurs when an "intruder" distance is below the threshold.

Figure 22:
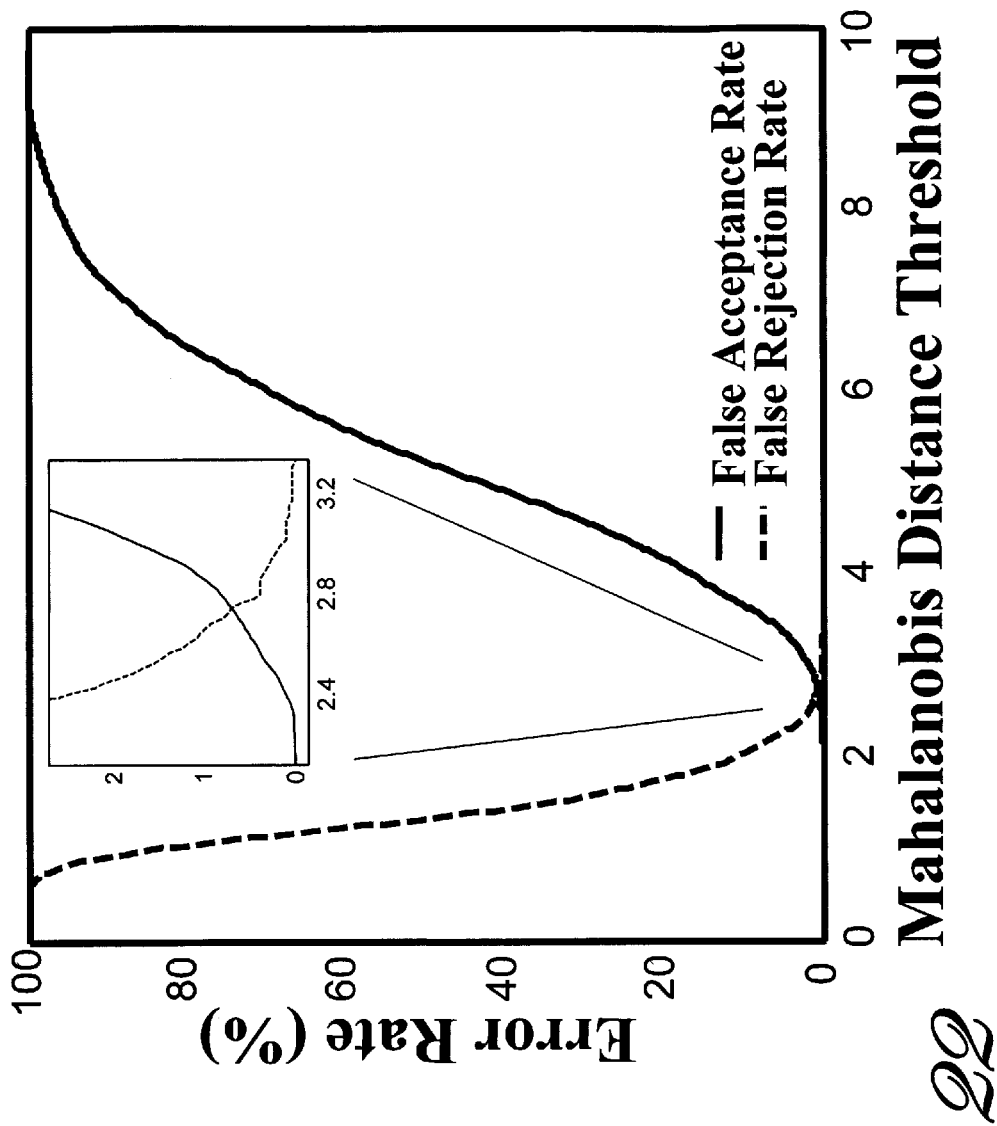
FIG. 22 shows the biometric verification false acceptance, false rejection, and equal error rates obtained using the spectroscopic method of the present invention in clinical studies.

The overall performance of a technique can be compactly summarized at a given threshold by calculating the "false acceptance rate" and the "false rejection rate". The false acceptance rate is the percentage of measurements acquired from intruders that are erroneously flagged as authorized. Conversely, the false rejection rate is the percentage of measurements acquired from authorized persons that are erroneously flagged as intruders. The threshold is a tunable variable that can be used to influence the relative security of the biometric measurement. For example, the threshold can be set to a low value (high security) that will minimize the false acceptance rate at the expense of an increase in the false rejection rate. Likewise, a low security setting would correspond to a high threshold value. In this scenario, authorized users would be rejected less frequently at the expense of an increase in intruder admission. FIG. 22 shows the false acceptance and false rejection rates at a variety of thresholds for the test data discussed above. The "equal error rate" occurs when the false acceptance and rejection rates are equal and is a common metric often used to compare biometric performance across techniques. The equal error rate for these data is approximately 0.7% demonstrating a high degree of biometric capability over an extended period of time.

What is claimed is:

1. An apparatus for initiating an action responsive to an individual entering or leaving or attempting to enter or leave a controlled environment, comprising:
   a) A spectroscopic system adapted to determine a spectroscopic signal from the response of at least a portion of the individual's tissue to incident electromagnetic radiation;
   b) An analysis system adapted to determine from the spectroscopic signal one or more analyte properties characteristic of the individual, wherein the analysis system is further adapted to determine an identity characteristic of the individual from the spectroscopic signal;
   c) An action initiation system adapted to initiate an action responsive to the one or more analyte properties, wherein the action initiation system is adapted to initiate an action responsive to both the identity characteristic and the one or more analyte properties.

2. An apparatus as in claim 1, wherein the one or more analyte properties comprises the presence of alcohol or one or more alcohol byproducts in the individual, the concentration of alcohol or one or more alcohol byproducts in the individual, or both.

3. An apparatus as in claim 1, wherein the action initiation system is adapted to communicate the one or more analyte properties to an agent associated with the controlled environment.

4. An apparatus as in claim 1, wherein the action initiation system is adapted to record the one or more analyte properties.

5. An apparatus as in claim 1, wherein the action initiation system is adapted to allow or disallow access to the controlled environment based on the one or more analyte properties.

6. An apparatus as in claim 1, wherein the action initiation system is adapted to communicate to an agent associated with the controlled environment the result of a comparison of the one or more analyte properties with predetermined values.

7. An apparatus as in claim 1, where the one or more analyte properties comprise the presence, concentration, or both of a substance of abuse in the individual.

8. An apparatus as in claim 1, where the spectroscopic system operates using one or more of: near infrared absorption spectroscopy, near infrared emission spectroscopy, infrared absorption spectroscopy, infrared emission spectroscopy, Raman spectroscopy, visible absorption spectroscopy, or fluorescence spectroscopy.

9. An apparatus as in claim 1, wherein the analysis system is adapted to determine at least one analyte property using multivariate analysis of the spectroscopic signal.

10. An apparatus as in claim 9, wherein the multivariate analysis comprises using a neural network, K-nearest neighbors, discriminant analysis, classification analysis, principal components analysis, partial least squares regression, classical least squares regression, logistic regression, nonlinear regression, or a combination thereof.

11. An apparatus as in claim 1, wherein the portion of the individual's tissue comprises at least one of: the finger, forearm, ear lobe, palm, lip, hand, or skin of the individual.

12. An apparatus as in claim 1, where the identity characteristic comprises verification or nonverification of the purported identity of the subject.

13. An apparatus as in claim 12, further comprising an identity input system comprising at least one of: an alphanumeric password entry device, a key input device, a magnetic swipe card reader, a GPS location device, a finger print reader, a voice recognition system, a retina scanner, bar code scanner, or an implanted sensor or material.

14. An apparatus as in claim 1, where the identity characteristic comprises determination of whether the individual is part of a predetermined group, without requiring the individual to indicate a purported identity.

15. An apparatus as in claim 14, where the authorized group consists of only one individual.

16. An apparatus as in claim 1, where the controlled environment or site is one of: a hospital, area of a hospital, surgical suite, prison, area of a prison, jail, health clinic, dental office, aircraft cockpit, airport terminal, area of an airport, automobile, a truck, a bus, parole office, probation office, court building, courtroom, home arrest location, residential treatment center, office building, warehouse, storage facility, office or offices within a building, factory, regions within a factory, construction site, sports facility, recreational facility, amusement park, school, school activity site, dormitory, restaurant, bar, club, day care facility, ship, military installation, roadside stop, traffic accident site, DUI checkpoint, train control room, train, research facilities, laboratories, maintenance facilities, classified facilities, air traffic control facility, security center, historic sites, parks, machine shop, dispatch office, dispatch center, garages, school bus faculties, or a power plant.

17. An apparatus as in claim 1, wherein the spectroscopic system comprises a dispersive spectrometer.

18. An apparatus as in claim 1, wherein the spectroscopic system comprises an interferometric/modulating spectrometer.

19. An apparatus as in claim 1, wherein the spectroscopic system comprises a combination of a dispersive spectrometer and an interferometric/modulating spectrometer.

20. An apparatus as in claim 1, wherein the analysis system is adapted to determine from the spectroscopic signal the presence of topical or chemical interferents.

21. An apparatus as in claim 20, wherein the analysis system is adapted to determine from the spectroscopic signal the presence of topical or chemical interferents by applying to the spectroscopic signal a model relating a spectroscopic signal to presence of an interferent, and from the result determining whether the spectrum indicates an interferent condition, and wherein the analysis system is adapted to determine the one or more analyte properties from the spectroscopic system and from the indicated interferent condition.

22. An apparatus as in claim 1, wherein the analysis system determines the one or more analyte properties in part by correcting, filtering, or adjusting the spectroscopic signal for topical or chemical interferents.

23. An apparatus as in claim 1, wherein the spectroscopic system is adapted to determine the response of the portion of tissue at a single distribution of path lengths through the portion of tissue.

24. An apparatus as in claim 1, wherein the spectroscopic system is adapted to determine the response of the portion of tissue at a first distribution of path lengths through the tissue, and at a second distribution of path lengths through the tissue, wherein the second distribution of path lengths is different from the first distribution of path lengths.

25. An apparatus as in claim 1, wherein the spectroscopic system comprises
   a) an illumination subsystem;
   b) a tissue sampling subsystem, in optical communication with the illumination subsystem;
   c) a spectrometer subsystem in optical communication with the tissue sampling subsystem, said spectrometer subsystem including a spectrometer;
   d) a data acquisition subsystem including a detector which receives an output from the spectrometer subsystem and converts said output to a communicable representation, said data acquisition subsystem including means for modifying said communicable representation and producing an analyzable representation thereof.

26. An apparatus as in claim 1, wherein the analysis system is adapted to determine at least one analyte property or identity characteristic using multivariate analysis of the spectroscopic signal.

27. An apparatus for monitoring compliance of an individual with requirements relating to the consumption of alcohol, comprising:
   a) A spectroscopic system adapted to determine a spectroscopic signal from the response of at least a portion of the individual's tissue to incident electromagnetic radiation;
   b) An analysis system adapted to determine from the spectroscopic signal the presence, concentration, or both, of alcohol or an alcohol byproduct in the individual's tissue and further adapted to determine an identity characteristic of the individual from the spectroscopic signal;
   c) An output system adapted to communicate a signal responsive to the determination of the analysis system.

28. An apparatus as in claim 27, wherein the analysis system compares a determined indication of alcohol concentration with a predetermined threshold indication of alcohol concentration, and wherein the output system communicates the result of that comparison.

29. An apparatus as in claim 28, wherein the output system activates an alert signal if the determined indication of alcohol concentration exceeds the predetermined threshold indication of alcohol concentration.

30. An apparatus as in claim 27, wherein the output system records in persistent storage the determination by the analysis system.

31. An apparatus as in claim 27, wherein the output system communicates to a remote location the determination of the analysis system.

32. A method of monitoring the sobriety of individuals entering a treatment facility, comprising determining and recording with an apparatus as in claim 27 the presence or concentration of alcohol in the tissue of an individual and an identity characteristic, and, if the alcohol concentration exceeds a predetermined threshold or the identity characteristic is deemed incorrect, communicating and recording an alert signal.

33. A method of controlling access to a workplace by individuals, comprising determining with an apparatus as in claim 27 the presence or concentration of alcohol in the tissue of an individual and the identity of the individual, and, if the alcohol concentration exceeds a predetermined threshold, communicating an indication that access to the workplace by that individual be denied.

34. A method of monitoring compliance of a monitored individual with requirements related to verifying sobriety, comprising determining with an apparatus as in claim 27 the presence or concentration of alcohol in the tissue of a testing individual and an identity characteristic of the testing individual, and, if the alcohol concentration exceeds a predetermined threshold then communicating a corresponding signal to a remote agent, and, if the identity characteristic of the testing individual does not match the identity of the monitored individual, then communicating a corresponding signal to a remote agent.

35. A method as in claim 34, further comprising, if a testing individual has not been determined to have an acceptable alcohol concentration and an identity characteristic matching that of the monitored individual within a predetermined time, then communicating a corresponding signal to a remote agent.

36. A system for monitoring compliance with requirements related to alcohol or substance of abuse consumption, comprising a plurality of apparatuses as in claim 27 disposed in a plurality of locations remote from each other, with each such apparatus connected to a communication system, wherein each such apparatus is adapted to communicate to a remote monitor the identity and the alcohol status of an individual presenting to the apparatus.

37. A method of remotely monitoring compliance of a plurality of individuals with requirements related to alcohol consumption, comprising disposing a plurality of apparatuses as in claim 27 in a plurality of locations remote from each other, determining with one of such apparatuses the identity and alcohol status of an individual presenting to the apparatus, and communicating the determined identity and determined alcohol status to a remote monitor, and wherein each of the plurality of individuals can present to any of the plurality of apparatuses.

38. A method of controlling access to a workplace by individuals, comprising determining with an apparatus as in claim 27 the presence or concentration of alcohol in the tissue of an individual and whether the individual belongs to a predetermined group of individuals, and, if the alcohol concentration exceeds a predetermined threshold or the individual does not belong to the predetermined group of individuals, then communicating an indication that access to the workplace by that individual be denied.

* * * * *